United States Patent
Ashton et al.

(10) Patent No.: US 7,956,061 B2
(45) Date of Patent: Jun. 7, 2011

(54) BICYCLIC PYRIMIDINES AS DIPEPTIDYL PEPTIDASE-IV INHIBITORS FOR THE TREATMENT OR PREVENTION OF DIABETES

(75) Inventors: Wallace T. Ashton, Edison, NJ (US); Charles G. Caldwell, Dallas, TX (US); Hong Dong, Livingston, NJ (US); Ying-Duo Gao, Edison, NJ (US); Giovanna Scapin, Staten Island, NY (US); Ann E. Weber, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 559 days.

(21) Appl. No.: 11/793,093

(22) PCT Filed: Jan. 18, 2006

(86) PCT No.: PCT/US2006/001660
§ 371 (c)(1),
(2), (4) Date: Oct. 26, 2007

(87) PCT Pub. No.: WO2006/078676
PCT Pub. Date: Jul. 27, 2006

(65) Prior Publication Data
US 2009/0105210 A1    Apr. 23, 2009

Related U.S. Application Data

(60) Provisional application No. 60/645,220, filed on Jan. 19, 2005.

(51) Int. Cl.
C07D 487/04 (2006.01)
A61K 31/519 (2006.01)
A61P 3/10 (2006.01)
(52) U.S. Cl. ............... 514/259.3; 544/281; 544/263
(58) Field of Classification Search ............... 544/281; 514/259.3
See application file for complete search history.

(56) References Cited

U.S. PATENT DOCUMENTS
2006/0178377 A1    8/2006    Meng et al.

FOREIGN PATENT DOCUMENTS
WO    2004/032836 A2    4/2004
WO    2004/032836 A3    4/2004

OTHER PUBLICATIONS

Abu Elmaai, T. M. et al., "Routes to Pyrazolo[3,4-e][1,4]thiazepine, Pyrazolo[1,5-a]pyrimidine and Pyrazole Derivatives" Journal of the Chinese Chemical Society, vol. 50, pp. 413-418, 2003.
Green, B. D. et al., "Inhibition of dipeptidyl peptidase IV activity as a therapy of Type 2 diabetes" Expert Opin. Emerging Drugs, vol. 11, No. 3, pp. 525-539, 2006.
Stonehouse, A. H. et al., "Management of Type 2 diabetes: the role of incretin mimetics" Expert Opin. Pharmacother, vol. 7, No. 15, pp. 2095-2105, 2006.
Combettes, M, MJ., "GLP-1 and type 2 diabetes: physiology and new clinical advances" Current Opinion in Pharmacology, vol. 6, pp. 598-605, 2006.
Holst, J. J. et al., "New Horizons in Diabetes Therapy" Immun., Endoc. & Metab. Agents in Med. Chem, vol. 7, pp. 49-55, 2007.
Campbell, R. K., "Rationale for Dipeptidyl Peptidase 4 Inhibitors: A New Class of Oral Agents for the Treatment of Type 2 Diabetes Mellitus" The Annals of Pharmacotherapy, vol. 41, pp. 51-60, 2007.

*Primary Examiner* — Susanna Moore
(74) *Attorney, Agent, or Firm* — Janet E. Fair; John C. Todaro

(57) ABSTRACT

The present invention is directed to novel substituted bicyclic pyrimidines which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

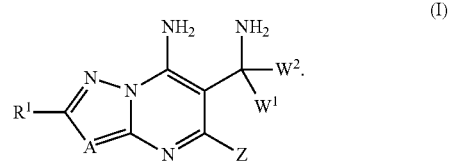

8 Claims, No Drawings

BICYCLIC PYRIMIDINES AS DIPEPTIDYL PEPTIDASE-IV INHIBITORS FOR THE TREATMENT OR PREVENTION OF DIABETES

CROSS REFERENCE TO RELATED APPLICATIONS

This application is the National Stage of International Application No. PCT/US2006/001660, filed 18 Jan. 2006, which claims the benefit under 35 U.S.C. 119(e) of U.S. Provisional Application No. 60/645,220, filed 19 Jan. 2005.

FIELD OF THE INVENTION

The present invention relates to novel substituted bicyclic pyrimidines which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for Type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e., 5-benzylthiazolidine-2,4-diones) are a more recently described class of compounds with potential for ameliorating many symptoms of Type 2 diabetes. These agents substantially increase insulin sensitivity in muscle, liver and adipose tissue in several animal models of Type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensitization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DPP-IV") enzyme are under investigation as drugs that may be useful in the treatment of diabetes, and particularly Type 2 diabetes. For a description of various structural classes of DPP-IV inhibitors, reference is made to international patent publications WO 97/40832; WO 98/19998; WO 01/68603; WO 02/38541; WO 02/076450; WO 03/000180; WO 03/000181; WO 03/024942; WO 03/033524; WO 03/035057; WO 03/035067; WO 03/037327; WO 03/074500; WO 03/082817; WO 04/007468; WO 04/018467; WO 04/026822; WO 04/032836; WO 04/037181; WO 04/041795; WO 04/043940; WO 04/046106; WO 04/050022; WO 04/058266; WO 04/064778; WO 04/069162; WO 04/071454; U.S. Pat. Nos. 5,939,560; 6,011,155; 6,107,317; 6,110,949; 6,166,063; 6,124,305; 6,303,661; 6,432,969; 6,617,340; and 6,699,871; *Bioorg. Med. Chem. Lett.*, 6: 1163-1166 (1996); and *Bioorg. Med. Chem. Lett.*, 6: 2745-2748 (1996). The usefulness of DPP-IV inhibitors in the treatment of Type 2 diabetes is based on the fact that DPP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DPP-IV leads to decreased inactivation of the incretins, and this in turn results in increased effectiveness of the incretins in stimulating production of insulin by the pancreas. DPP-IV inhibition therefore results in an increased level of serum insulin. Advantageously, since the incretins are produced by the body only when food is consumed, DPP-IV inhibition is not expected to increase the level of insulin at inappropriate times, such as between meals, which can lead to excessively low blood sugar (hypoglycemia). Inhibition of DPP-IV is therefore expected to increase insulin without increasing the risk of hypoglycemia, which is a dangerous side effect associated with the use of insulin secretagogues.

DPP-IV inhibitors also have other therapeutic utilities, as discussed herein. DPP-IV inhibitors have not been studied extensively for utilities other than diabetes. New compounds are needed so that improved DPP-IV inhibitors can be found for the treatment of diabetes and potentially other diseases and conditions. The therapeutic potential of DPP-IV inhibitors for the treatment of Type 2 diabetes is discussed by D. J. Drucker in *Exp. Opin. Invest. Drugs*, 12: 87-100 (2003); by K. Augustyns, et al., in *Exp. Opin. Ther. Patents*, 13: 499-510 (2003); and by C. F. Deacon, et al., in *Exp. Opin. Investig. Drugs*, 13: 1091-1102 (2004).

SUMMARY OF THE INVENTION

The present invention is directed to novel substituted bicyclic pyrimidines which are inhibitors of the dipeptidyl peptidase-IV enzyme ("DPP-IV inhibitors") and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to substituted bicyclic pyrimidines that are useful as inhibitors of dipeptidyl peptidase-IV. Compounds of the present invention are described by structural formula I:

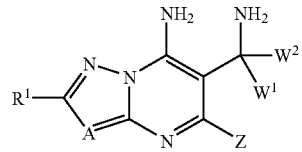

(I)

and pharmaceutically acceptable salts thereof; wherein
each n is independently 0, 1, 2, or 3;
A is N or $CR^2$;
$W^1$ and $W^2$ are independently H or $C_{1-4}$ alkyl; or $W^1$ and $W^2$ together with the carbon atom to which they are attached form a 3- to 6-membered carbocyclic ring;
Z is phenyl or pyridyl, each of which is substituted with one to five $R^3$ substitutents;
$R^1$ and $R^2$ are each independently selected from the group consisting of:
  (1) hydrogen,
  (2) $C_{1-10}$ alkyl, wherein alkyl is unsubstituted or substituted with one to five substituents independently selected from:
    (a) halogen,
    (b) hydroxy,
    (c) $OR^4$,
    (d) $SR^4$,
    (e) $S(O)_{1-2}R^4$,
    (f) $SO_2NR^5R^6$,
    (g) $NR^5R^6$,
    (h) $NHSO_2R^4$,
    (i) $N(C_{1-6}\ alkyl)SO_2R^4$,
    (j) $NHCONR^5R^6$,
    (k) $N(C_{1-6}\ alkyl)CONR^5R^6$,
    (l) $NHCO_2R^4$,
    (m) $N(C_{1-6}\ alkyl)CO_2R^4$,
    (n) $OCONR^5R^6$,
    (o) CN,
    (p) $CO_2H$,
    (q) $CO_2C_{1-6}$ alkyl,
    (r) $CONR^5R^6$, and
    (s) phenyl, which is unsubstituted or substituted with one to five substituents independently selected from halogen, CN, OH, $R^4$, $OR^4$, $NHSO_2R^4$, $N(C_{1-6}\ alkyl)SO_2R^4$, $SO_2R^4$, $SO_2NR^5R^6$, $NR^5R^6$, $CONR^5R^6$, $CO_2H$, and $CO_2C_{1-6}$ alkyl,
  (3) phenyl, wherein phenyl is unsubstituted or substituted with one to five substituents independently selected from halogen, $R^4$, OH, $OR^4$, $NHSO_2R^4$, $N(C_{1-6}\ alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
  (4) $(CH_2)_n$-heteroaryl, wherein heteroaryl is unsubstituted or substituted with one to three substituents independently selected from halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
  (5) $(CH_2)_n$-heterocyclyl, wherein heterocyclyl is unsubstituted or substituted with one to three substituents independently selected from oxo, halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
  (6) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy, wherein alkyl and alkoxy are unsubstituted or substituted with one to five halogens,
  (7) hydroxy,
  (8) $OR^4$,
  (9) $SR^4$,
  (10) $S(O)_{1-2}R^4$,
  (11) $SO_2NR^5R^6$,
  (12) $NR^5R^6$,
  (13) $NHSO_2R^4$,
  (14) $N(C_{1-6}\ alkyl)SO_2R^4$,
  (15) $NHCONR^5R^6$,
  (16) $N(C_{1-6}\ alkyl)CONR^5R^6$,
  (17) $NHCO_2R^4$,
  (18) $N(C_{1-6}\ alkyl)CO_2R^4$,
  (19) $OCONR^5R^6$,
  (20) CN,
  (21) $CO_2H$,
  (22) $CO_2C_{1-6}$ alkyl,
  (23) $CONR^5R^6$, and
  (24) halogen;
or wherein $R^1$ and $R^2$ together with the carbon atoms to which they are attached form a 5- to 6-membered aromatic, heteroaryl, carbocyclic, or heterocyclic ring; wherein said ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

each $R^3$ is independently selected from the group consisting of:
(1) halogen,
(2) $C_{1-6}$ alkyl, unsubstituted or substituted with one to five substituents independently selected from halogen, hydroxy, and $C_{1-4}$ alkoxy,
(3) $C_{1-6}$ alkoxy, unsubstituted or substituted with one to five substituents independently selected from halogen, hydroxy, and $C_{1-4}$ alkoxy,
(4) hydroxy,
(5) $O(CH_2)_n$-aryl, wherein aryl is unsubstituted or substituted with one to five substituents independently selected from halogen, methyl, hydroxy, and methoxy, and
(6) $O(CH_2)_n$-heteroaryl, wherein heteroaryl is unsubstituted or substituted with one to five substituents independently selected from halogen, methyl, hydroxy, and methoxy;

$R^4$ is $C_{1-6}$ alkyl, unsubstituted or substituted with one to five substituents independently selected from halogen, hydroxy, methoxy, $CO_2H$, and $CO_2C_{1-6}$ alkyl; and $R^5$ and $R^6$ are each independently selected from the group consisting of:
(1) hydrogen,
(2) $C_{1-6}$ alkyl, unsubstituted or substituted with one to five substituents independently selected from halogen, hydroxy, and $C_{1-6}$ alkoxy,
(3) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy, wherein alkyl and alkoxy are unsubstituted or substituted with one to five halogens, and
(4) $(CH_2)_n$-phenyl, wherein phenyl is unsubstituted or substituted with substituents independently selected from halogen, OH, $C_{1-6}$ allyl, and $C_{1-6}$ alkoxy, wherein alkyl and alkoxy are unsubstituted or substituted with one to five halogens;

or wherein $R^5$ and $R^6$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

In one embodiment of the compounds of the present invention, A is N as depicted in structural formula Ia:

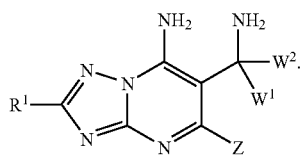

Ia

In a class of this embodiment, $W^1$ and $W^2$ are H, and $R^1$ and Z are as defined above.

In a subclass of this class, Z is phenyl which is substituted with two to five $R^3$ substituents;
each n is independently 0, 1, 2, or 3;

$R^1$ is selected from the group consisting of:
(1) hydrogen,
(2) $C_{1-4}$ alkyl, wherein alkyl is unsubstituted or substituted with one to five substituents independently selected from:
  (a) halogen,
  (b) hydroxy,
  (c) $OR^4$,
  (d) $SR^4$, and
  (e) $NR^5R^6$,
(3) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy,
(4) hydroxy,
(5) $OR^4$,
(6) $SR^4$, and
(7) $NR^5R^6$;

each $R^3$ is independently selected from the group consisting of:
(1) halogen,
(2) $C_{1-4}$ alkyl, unsubstituted or substituted with one to five substituents independently selected from halogen, hydroxy, and $C_{1-4}$ alkoxy,
(3) $C_{1-4}$ alkoxy, unsubstituted or substituted with one to five substituents independently selected from halogen, hydroxy, and $C_{1-4}$ alkoxy,
(4) hydroxy,
(5) $O(CH_2)_n$-aryl, wherein aryl is unsubstituted or substituted with one to five substituents independently selected from halogen, methyl, hydroxy, and methoxy, and
(6) $O(CH_2)_n$-heteroaryl, wherein heteroaryl is unsubstituted or substituted with one to five substituents independently selected from halogen, methyl, hydroxy, and methoxy;

$R^4$ is $C_{1-6}$ alkyl, unsubstituted or substituted with one to five substituents independently selected from halogen, hydroxy, and methoxy; and $R^5$ and $R^6$ are each independently selected from the group consisting of:
(1) hydrogen,
(2) $C_{1-4}$ alkyl, unsubstituted or substituted with one to five substituents independently selected from halogen, hydroxy, and $C_{1-4}$ alkoxy, and
(3) $(CH_2)_n$—$C_{3-6}$ cycloalkyl, wherein cycloalkyl is unsubstituted or substituted with one to five substituents independently selected from halogen, OH, $C_{1-4}$ alkyl, and $C_{1-4}$ alkoxy, wherein alkyl and alkoxy are unsubstituted or substituted with one to five halogens;

or wherein $R^5$ and $R^6$ together with the nitrogen atom to which they are attached form a heterocyclic ring selected from azetidine, pyrrolidine, piperidine, piperazine, and morpholine.

In a second embodiment of the compounds of the present invention, A is $CR^2$ as depicted in structural formula Ib:

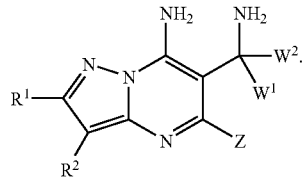

In a class of this embodiment, $W^1$ and $W^2$ are H, and $R^1$, $R^2$, and Z are as defined above.

In a subclass of this class, Z is phenyl which is substituted with two to five $R^3$ substituents;
each n is independently 0, 1, 2, or 3;
$R^1$ is selected from the group consisting of:
(1) hydrogen,
(2) $C_{1-4}$ alkyl, wherein alkyl is unsubstituted or substituted with one to five substituents independently selected from:
 (a) halogen,
 (b) hydroxy,
 (c) $OR^4$,
 (d) $SR^4$, and
 (e) $NR^5R^6$,
(3) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy,
(4) hydroxy,
(5) $OR^4$,
(6) $SR^4$, and
(7) $NR^5R^6$;
$R^2$ is selected from the group consisting of:
(1) hydrogen,
(2) $C_{10}$ alkyl, wherein alkyl is unsubstituted or substituted with one to five substituents independently selected from:
 (a) halogen,
 (b) hydroxy,
 (c) $OR^4$,
 (d) $SR^4$,
 (e) $S(O)_{1-2}R^4$,
 (f) $SO_2NR^5R^6$,
 (g) $NR^5R^6$,
 (h) $NHSO_2R^4$,
 (i) $N(C_{1-6}alkyl)SO_2R^4$,
 (j) $NHCONR^5R^6$,
 (k) $N(C_{1-6}\,alkyl)CONR^5R^6$,
 (l) $NHCO_2R^4$,
 (m) $N(C_{1-6}\,alkyl)CO_2R^4$,
 (n) $OCONR^5R^6$,
 (o) CN,
 (p) $CO_2H$,
 (q) $CO_2C_{1-6}$ alkyl,
 (r) $CONR^5R^6$, and
 (s) phenyl, which is unsubstituted or substituted with one to five substituents independently selected from halogen, CN, OH, $R^4$, $OR^4$, $NHSO_2R^4$, $N(C_{1-6}\,alkyl)SO_2R^4$, $SO_2R^4$, $SO_2NR^5R^6$, $NR^5R^6$, $CONR^5R^6$, $CO_2H$, and $CO_2C_{1-6}$ alkyl,
(3) phenyl which is unsubstituted or substituted with one to five substituents independently selected from halogen, $R^4$, OH, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(4) $(CH_2)_n$-heteroaryl, wherein heteroaryl is unsubstituted or substituted with one to three substituents independently selected from halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(5) $(CH_2)_n$-heterocyclyl, wherein heterocyclyl is unsubstituted or substituted with one to three substituents independently selected from oxo, halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(6) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy, wherein alkyl and alkoxy are unsubstituted or substituted with one to five halogens,
(7) hydroxy,
(8) $OR^4$,
(9) $SR^4$,
(10) $S(O)_{1-2}R^4$,
(11) $SO_2NR^5R^6$,
(12) $NR^5R^6$,
(13) $NHSO_2R^4$,
(14) $N(C_{1-6}alkyl)SO_2R^4$,
(15) $NHCONR^5R^6$,
(16) $N(C_{1-6}\,alkyl)CONR^5R^6$,
(17) $NHCO_2R^4$,
(18) $N(C_{1-6}\,alkyl)CO_2R^4$,
(19) $OCONR^5R^6$,
(20) CN,
(21) $CO_2H$,
(22) $CO_2C_{1-6}$ alkyl,
(23) $CONR^5R^6$, and
(24) halogen,
or wherein $R^1$ and $R^2$ together with the carbon atoms to which they are attached form a 5-6 membered aromatic, heteroaryl, carbocyclic, or heterocyclic ring;
each $R^3$ is independently selected from the group consisting of:
(1) halogen,
(2) $C_{1-4}$ alkyl, unsubstituted or substituted with one to five substituents independently selected from halogen, hydroxy, and $C_{1-4}$ alkoxy,
(3) $C_{1-4}$ alkoxy, unsubstituted or substituted with one to five substituents independently selected from halogen, hydroxy, and $C_{1-4}$ alkoxy,
(4) hydroxy,
(5) $O(CH_2)_n$-aryl, wherein aryl is unsubstituted or substituted with one to five substituents independently selected from halogen, methyl, hydroxy, and methoxy, and
(6) $O(CH_2)_n$-heteroaryl, wherein heteroaryl is unsubstituted or substituted with one to five substituents independently selected from halogen, methyl, hydroxy, and methoxy;
$R^4$ is $C_{1-6}$ alkyl, unsubstituted or substituted with one to five substituents independently selected from halogen, hydroxy, and methoxy; and
$R^5$ and $R^6$ are independently selected from the group consisting of:
(1) hydrogen,
(2) $C_{1-4}$ alkyl, unsubstituted or substituted with one to five substituents independently selected from halogen, hydroxy, and $C_{1-4}$ alkoxy, and (3) $(CH_2)_n$—$C_{3-6}$ cycloalkyl, wherein cycloalkyl is unsubstituted or substituted with one to five substituents independently selected from halogen, OH, $C_{1-4}$ alkyl, and $C_{1-4}$ alkoxy, wherein alkyl and alkoxy are unsubstituted or substituted with one to five halogens;

or wherein $R^5$ and $R^6$ together with the nitrogen atom to which they are attached form a heterocyclic ring selected from azetidine, pyrrolidine, piperidine, piperazine, and morpholine.

In a further embodiment of the compounds in the present invention, $W^1$ and $W^2$ are H as depicted in structural formula Ic:

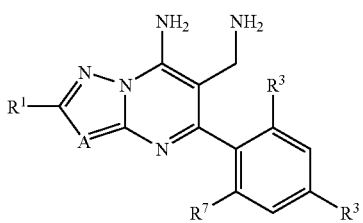

Ic wherein each n is independently 0, 1, 2, or 3;

A is N or $CR^2$;

$R^3$ is chloro or methyl, which is unsubstituted or substituted with one to three fluorine atoms;

$R^7$ is selected from the group consisting of:
(1) hydrogen,
(2) halogen,
(3) $C_{1-6}$ alkyl, unsubstituted or substituted with one to five substituents independently selected from halogen, hydroxy, and $C_{1-4}$ alkoxy,
(4) $C_{1-6}$ alkoxy, unsubstituted or substituted with one to five substituents independently selected from halogen, hydroxy, and $C_{1-4}$ alkoxy,
(5) hydroxy,
(6) $O(CH_2)_n$-aryl, wherein aryl is unsubstituted or substituted with one to five substituents independently selected from halogen, methyl, hydroxyl, and methoxy, and
(7) $O(CH_2)_n$-heteroaryl, wherein heteroaryl is unsubstituted or substituted with one to five substituents independently selected from halogen, methyl, hydroxyl, and methoxy;

$R^1$ is selected from the group consisting of:
(1) hydrogen,
(2) $C_{1-4}$ alkyl, wherein alkyl is unsubstituted or substituted with one to five substituents independently selected from:
(a) halogen,
(b) hydroxy,
(c) $OR^4$,
(d) $SR^4$, and
(e) $NR^5R^6$,
(3) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy,
(4) hydroxy,
(5) $OR^4$,
(6) $SR^4$, and
(7) $NR^5R^6$; and $R^2$ is selected from the group consisting of:
(1) hydrogen,
(2) $C_{1-10}$ alkyl, wherein alkyl is unsubstituted or substituted with one to five substituents independently selected from:
(a) halogen,
(b) hydroxy,
(c) $OR^4$,
(d) $SR^4$,
(e) $S(O)_{1-2}R^4$,
(f) $SO_2NR^5R^6$,
(g) $NR^5R^6$,
(h) $NHSO_2R^4$,
(i) $N(C_{1-6}alkyl)SO_2R^4$,
(j) $NHCONR^5R^6$,
(k) $N(C_{1-6} alkyl)CONR^5R^6$,
(l) $NHCO_2R^4$,
(m) $N(C_{1-6} alkyl)CO_2R^4$,
(n) $OCONR^5R^6$,
(o) CN,
(p) $CO_2H$,
(q) $CO_2C_{1-6}$ alkyl,
(r) $CONR^5R^6$, and
(s) phenyl, which is unsubstituted or substituted with one to five substituents independently selected from halogen, CN, OH, $R^4$, $OR^4$, $NHSO_2R^4$, $N(C_{1-6}$ alkyl)$SO_2R^4$, $SO_2R^4$, $SO_2NR^5R^6$, $NR^5R^6$, $CONR^5R^6$, $CO_2H$, and $CO_2C_{1-6}$ alkyl,
(3) phenyl which is unsubstituted or substituted with one to five substituents independently selected from halogen, $R^4$, OH, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(4) $(CH_2)_n$-heteroaryl, wherein heteroaryl is unsubstituted or substituted with one to three substituents independently selected from halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(5) $(CH_2)_n$-heterocyclyl, wherein heterocyclyl is unsubstituted or substituted with one to three substituents independently selected from oxo, halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(6) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy, wherein alkyl and alkoxy are unsubstituted or substituted with one to five halogens,
(7) hydroxy,
(8) $OR^4$,
(9) $SR^4$,
(10) $S(O)_{1-2}R^4$,
(11) $SO_2NR^5R^6$,
(12) $NR^5R^6$,
(13) $NHSO_2R^4$,
(14) $N(C_{1-6}alkyl)SO_2R^4$,
(15) $NHCONR^5R^6$,
(16) $N(C_{1-6} alkyl)CONR^5R^6$,
(17) $NHCO_2R^4$,
(18) $N(C_{1-6} alkyl)CO_2R^4$,
(19) $OCONR^5R^6$,
(20) CN,
(21) $CO_2H$,
(22) $CO_2C_{1-6}$ alkyl,
(23) $CONR^5R^6$, and
(24) halogen;

or wherein $R^1$ and $R^2$ together with the carbon atoms to which they are attached form a five to six-membered aromatic, heteroaryl, carbocyclic, or heterocyclic ring.

Illustrative, but nonlimiting, examples of compounds of the present invention that are useful as DPP-IV inhibitors are the following structures and pharmaceutically acceptable salts thereof:

6-(aminomethyl)-5-mesityl-3-methylpyrazolo[1,5-a]pyrimidin-7-amine

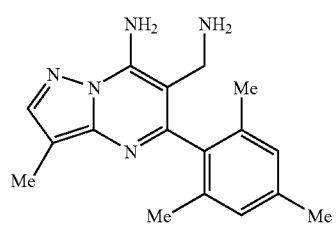

6-(aminomethyl)-5-mesityl-3-methoxypyrazolo[1,5-a]pyrimidin-7-amine

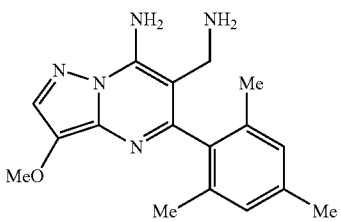

6-(aminomethyl)-5-(2,4-dichlorophenyl)[1,2,4]triazolo[1,5-a]pyrimidin-7-amine

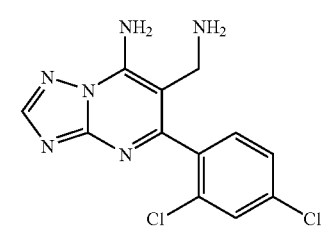

6-(aminomethyl)-2-cyclopropyl-5-mesityl[1,2,4]triazolo[1,5-a]pyrimidin-7-amine

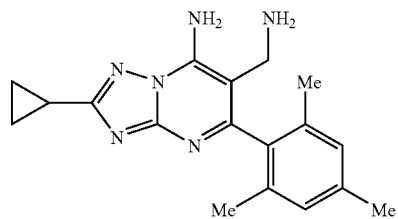

6-(aminomethyl)-5-mesityl[1,2,4]triazolo[1,5-a]pyrimidine-2,7-diamine

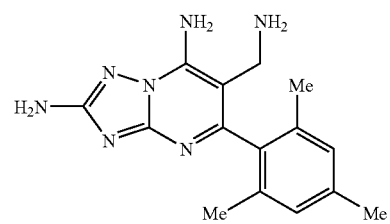

6-(aminomethyl)-5-(2,4-dichlorophenyl)[1,2,4]triazolo[1,5-a]pyrimidine-2,7-diamine

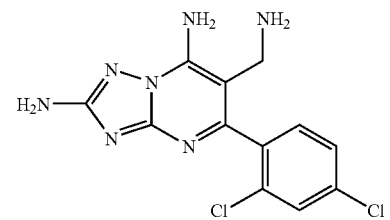

6-(aminomethyl)-5-(2,4,6-trichlorophenyl)[1,2,4]triazolo[1,5-a]pyrimidine-2,7-diamine

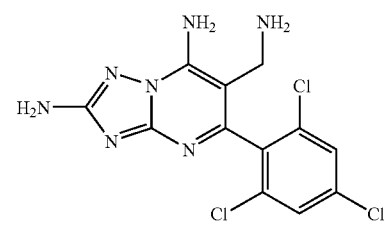

6-(aminomethyl)-5-mesityl[1,2,4]triazolo[1,5-a]pyrimidin-7-amine

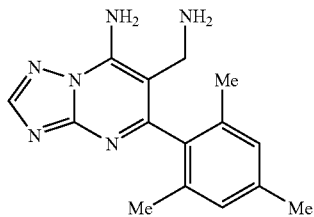

6-(aminomethyl)-5-(2,4,6-trichlorophenyl)[1,2,4]triazolo[1,5-a]pyrimidin-7-amine

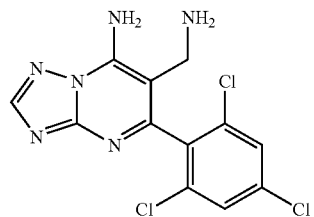

6-(aminomethyl)-5-(2,4-dimethylphenyl)-3-methylpyrazolo[1,5-a]pyrimidin-7-amine

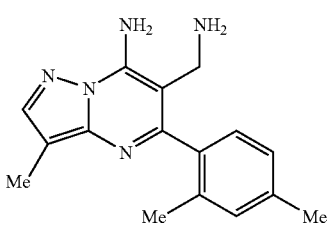

6-(aminomethyl)-3-methyl-5-(2,4,6-trichlorophenyl)pyrazolo[1,5-a]pyrimidin-7-amine

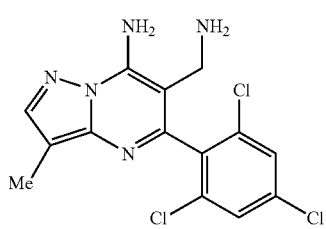

6-(aminomethyl)-5-mesityl-2,3-dimethylpyrazolo[1,5-a]pyrimidin-7-amine

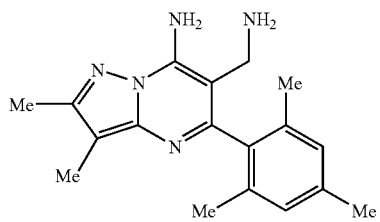

6-(aminomethyl)-5-(2,4,6-trichlorophenyl)pyrazolo[1,5-a]pyrimidin-7-amine

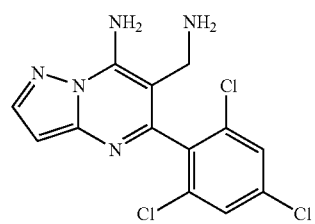

[7-amino-6-(aminomethyl)-5-mesityl[1,2,4]triazolo[1,5-a]pyrimidin-2-yl]methanol

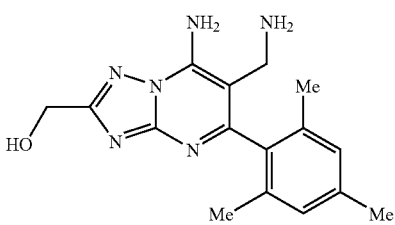

and 6-(aminomethyl)-5-mesityl-2-(methylthio)pyrazolo[1,5-a]pyrimidin-7-amine

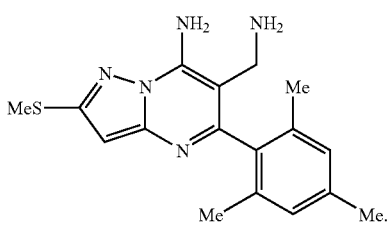

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

The term "cycloalkyl" refers to a saturated hydrocarbon containing one ring having a specified number of carbon atoms. Examples of cycloalkyl include cyclopropyl (cPr), cyclobutyl, cyclopentyl, cyclohexyl, cycloheptyl, cyclooctyl, and the like. A cycloalkyl group is monocyclic unless stated otherwise. Cycloalkyl groups are saturated unless otherwise defined.

The term "alkoxy" refers to straight or branched chain alkoxides of the number of carbon atoms specified (e.g., $C_{1-10}$ alkoxy), or any number within this range [i.e., methoxy (MeO—), ethoxy, isopropoxy, etc.].

The term "alkylthio" refers to straight or branched chain allylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6-10 membered aromatic ring systems. Phenyl and naphthyl are preferred aryls. The most preferred aryl is phenyl.

The term "heterocyclyl" refers to saturated or unsaturated non-aromatic rings or ring systems containing at least one heteroatom selected from O, S and N, further including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, pyrrolidinone, oxazolidin-2-one, imidazolidine-2-one, pyridone, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxypyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-a]pyridinyl, [1,2,4-triazolo][4,3-a]pyridinyl, pyrazolo[1,5-a]pyridinyl, [1,2,4-triazolo][1,5-a]pyridinyl, 2-oxo-1,3-benzoxazolyl, 4-oxo-3H-quinazolinyl, 3-oxo-[1,2,4]-triazolo[4,3-a]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, imidazo[1,2-a]pyrimidinyl, imidazo[1,5-a]pyrimidinyl, pyrazolo[1,5-a]pyrimidinyl, [1,2,4-triazolo][1,5-a]pyrimidinyl, [1,2,4-triazolo][4,3-a]pyrimidinyl, [1,2,3-triazolo][1,5-a]pyrimidinyl, pyrazolo[1,5-b]pyridazinyl, imidazo[1,5-b]pyridazinyl, imidazo[1,2-b]pyridazinyl, [1,2,4-triazolo][4,3-b]pyridazinyl, [1,2,4-triazolo][1,5-b]pyridazinyl, pyrido[2,3-b]pyrazinyl, pyrido[3,2-d]pyrimidinyl, pyrido[2,3-d]pyrimidinyl, and the like. For heterocyclyl and heteroaryl groups, rings and ring systems containing from 3-15 atoms are included, forming 1-3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_3O$ and $CF_3CH_2O$).

The compounds of the present invention contain one or more asymmetric centers and can thus occur as racemates, racemic mixtures, single enantiomers, diastereomeric mixtures, and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent, such as a mouse, species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent. More particularly, the present invention is directed to the use of a compound of structural formula I in the manufacture of a medicament for use in treating a condition selected from the group consisting of hyperglycemia, Type 2 diabetes, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DPP-IV to release the fluorescent AMC leaving group. The kinetic parameters that describe this reaction are as follows: $K_m = 50$ μM; $k_{cat} = 75$ $s^{-1}$; $k_{cat}/K_m = 1.5 \times 10^6$ $M^{-1}$ $s^{-1}$. A typical reaction contains approximately 50 μM enzyme, 50 μM Gly-Pro-AMC, and buffer (100 mM HEPES, pH 7.5, 0.1 mg/ml BSA) in a total reaction volume of 100 μl. Liberation of AMC is monitored continuously in a 96-well plate fluorometer using an excitation wavelength of 360 nm and an emission wavelength of 460 nm. Under these conditions, approximately 0.8 μM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 μM. Such a result is indicative of the intrinsic activity of the compounds in use as inhibitors the dipeptidyl peptidase-IV enzyme activity.

Dipeptidyl peptidase-IV enzyme (DPP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DPP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type II Diabetes and Related Disorders: It is well established that the incretins GLP-1 and GIP are rapidly inactivated in vivo by DPP-IV. Studies with DPP-IV$^{(-/-)}$-deficient mice and preliminary clinical trials indicate that DPP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DPP-IV (e.g. PACAP). Inactivation of these peptides by DPP-IV may also play a role in glucose homeostasis. The DPP-IV inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DPP-IV inhibitors may also be useful to treat hypertension associated with this condition.

Obesity: DPP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine* 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DPP-IV. ICV administration of GLP-2 also inhibits food intake, analogous to the effects observed with GLP-1 (*Nature Medicine*, 6: 802-807 (2000)). In addition, studies with DPP-IV deficient mice suggest that these animals are resistant to diet-induced obesity and associated pathology (e.g. hyperinsulinemia).

Cardiovascular Disease: GLP-1 has been shown to be beneficial when administered to patients following acute myocardial infarction, leading to improved left ventricular function and reduced mortality after primary angioplasty (*Circulation*, 109: 962-965 (2004)). GLP-1 administration is also useful for the treatment of left ventricular systolic dysfunction in dogs with dilated cardiomyopathy and ischemic induced left ventricular dysfunction, and thus may prove useful for the treatment of patients with heart failure (US2004/0097411). DPP-IV inhibitors are expected to show similar effects through their ability to stabilize endogenous GLP-1.

Growth Hormone Deficiency: DPP-IV inhibition may be useful for the treatment of growth hormone deficiency, based on the hypothesis that growth-hormone releasing factor (GRF), a peptide that stimulates release of growth hormone from the anterior pituitary, is cleaved by the DPP-IV enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DPP-IV inhibitor diprotin A; and (3) GRF[3-44] is found in the plasma of a human GRF transgenic pig (*J. Clin. Invest.*, 83: 1533-1540 (1989)). Thus DPP-IV inhibitors may be useful for the same spectrum of indications which have been considered for growth hormone secretagogues.

Intestinal Injury: The potential for using DPP-IV inhibitors for the treatment of intestinal injury is suggested by the results of studies indicating that glucagon-like peptide-2 (GLP-2), a likely endogenous substrate for DPP-IV, may exhibit trophic effects on the intestinal epithelium (*Regulatory Peptides* 90: 27-32 (2000)). Administration of GLP-2 results in increased small bowel mass in rodents and attenuates intestinal injury in rodent models of colitis and enteritis.

Immunosuppression: DPP-IV inhibition may be useful for modulation of the immune response, based upon studies implicating the DPP-IV enzyme in T cell activation and in chemokine processing, and efficacy of DPP-IV inhibitors in in vivo models of disease. DPP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DPP-IV. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DPP-IV hydrolysis.

DPP-IV inhibitors have been shown to be efficacious immunosuppressants in animal models of transplantation and arthritis. Prodipine (Pro-Pro-diphenyl-phosphonate), an irreversible inhibitor of DPP-IV, was shown to double cardiac allograft survival in rats from day 7 to day 14 (*Transplantation*, 63: 1495-1500 (1997)). DPP-IV inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DPP-IV is upregulated in a number of autoimmune diseases including rheumatoid arthritis, multiple sclerosis, Graves' disease, and Hashimoto's thyroiditis (*Immunology Today*, 20: 367-375 (1999)).

HIV Infection: DPP-IV inhibition may be useful for the treatment or prevention of HIV infection or AIDS because a number of chemokines which inhibit HIV cell entry are potential substrates for DPP-IV (*Immunology Today* 20: 367-375 (1999)). In the case of SDF-1alpha, cleavage decreases antiviral activity (*PNAS*, 95: 6331-6 (1998)). Thus, stabilization of SDF-1 alpha through inhibition of DPP-IV would be expected to decrease HIV infectivity.

Hematopoiesis: DPP-IV inhibition may be useful for the treatment or prevention of hematopoiesis because DPP-IV may be involved in hematopoiesis. A DPP-IV inhibitor, Val-Boro-Pro, stimulated hematopoiesis in a mouse model of cyclophosphamide-induced neutropenia (WO 99/56753).

Neuronal Disorders: DPP-IV inhibition may be useful for the treatment or prevention of various neuronal or psychiatric disorders because a number of peptides implicated in a variety of neuronal processes are cleaved in vitro by DPP-IV. A DPP-IV inhibitor thus may have a therapeutic benefit in the treatment of neuronal disorders. Endomorphin-2, beta-casomorphin, and substance P have all been shown to be in vitro substrates for DPP-IV. In all cases, in vitro cleavage is highly efficient, with $k_{cat}/K_m$ about $10^6$ $M^{-1}$ $s^{-1}$ or greater. In an electric shock jump test model of analgesia in rats, a DPP-IV inhibitor showed a significant effect that was independent of the presence of exogenous endomorphin-2 (*Brain Research*, 815: 278-286 (1999)). Neuroprotective and neuroregenerative effects of DPP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety: Rats naturally deficient in DPP-IV have an anxiolytic phenotype (WO 02/34243; Karl et al., *Physiol. Behav.* 2003). DPP-IV deficient mice also have an anxiolytic phenotype using the porsolt and light/dark models. Thus DPP-IV inhibitors may prove useful for treating anxiety and related disorders.

Memory and Cognition: GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DPP-IV inhibitors are expected to show similar effects.

Myocardial Infarction: GLP-1 has been shown to be beneficial when administered to patients following acute myocardial infarction (*Circulation*, 109: 962-965 (2004)). DPP-IV inhibitors are expected to show similar effects through their ability to stabilize endogenous GLP-1.

Tumor Invasion and Metastasis: DPP-IV inhibition may be useful for the treatment or prevention of tumor invasion and metastasis because an increase or decrease in expression of several ectopeptidases including DPP-IV has been observed during the transformation of normal cells to a malignant phenotype (*J. Exp. Med.*, 190: 301-305 (1999)). Up- or down-regulation of these proteins appears to be tissue and cell-type specific. For example, increased CD26/DPP-IV expression has been observed on T cell lymphoma, T cell acute lymphoblastic leukemia, cell-derived thyroid carcinomas, basal cell carcinomas, and breast carcinomas. Thus, DPP-IV inhibitors may have utility in the treatment of such carcinomas.

Benign Prostatic Hypertrophy: DPP-IV inhibition may be useful for the treatment of benign prostatic hypertrophy because increased DPP-IV activity was noted in prostate tissue from patients with BPH (*Eur. J. Clin. Chem. Clin. Biochem.* 30: 333-338 (1992)).

Sperm motility/male contraception: DPP-IV inhibition may be useful for the altering sperm motility and for male contraception because in seminal fluid, prostatosomes, prostate derived organelles important for sperm motility, possess very high levels of DPP-IV activity (*Eur. J. Clin. Chem. Clin. Biochem.*, 30: 333-338 (1992)).

Gingivitis: DPP-IV inhibition may be useful for the treatment of gingivitis because DPP-IV activity was found in gingival crevicular fluid and in some studies correlated with periodontal disease severity (*Arch. Oral Biol.*, 37: 167-173 (1992)).

Osteoporosis: DPP-IV inhibition may be useful for the treatment or prevention of osteoporosis because GIP receptors are present in osteoblasts.

Stem Cell Transplantation: Inhibition of DPP-IV on donor stem cells has been shown to lead to an enhancement of their bone marrow homing efficiency and engraftment, and an increase in survival in mice (Christopherson, et al., *Science*, 305:1000-1003 (2004)). Thus DPP-IV inhibitors may be useful in bone marrow transplantation.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type II diabetes, (26) growth hormone deficiency, (27) neutropenia, (28) neuronal disorders, (29) tumor metastasis, (30) benign prostatic hypertrophy, (31) gingivitis, (32) hypertension, (33) osteoporosis, and other conditions that may be treated or prevented by inhibition of DPP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DPP-IV) inhibitors;

(b) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual agonists, such as KRP-297, muraglitazar, naveglitazar, tesaglitazar, TAK-559, PPARα agonists, such as fenofibric acid derivatives (gemfibrozil, clofibrate, fenofibrate and bezafibrate), and selective PPARγ modulators (SPPARγM's), such as disclosed in WO 02/060388, WO 02/08188, WO 2004/019869, WO 2004/020409, WO 2004/020408, and WO 2004/066963; (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide, glyburide, glipizide, glimepiride, and meglitinides, such as nateglinide and repaglinide;

(e) α-glucosidase inhibitors (such as acarbose and miglitol);

(f) glucagon receptor antagonists, such as those disclosed in WO 97/16442; WO 98/04528, WO 98/21957; WO 98/22108; WO 98/22109; WO 99/01423, WO 00/39088, and WO 00/69810; WO 2004/050039; and WO 2004/069158;

(g) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(h) GIP and GIP mimetics, such as those disclosed in WO 00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO 97/28149;

(l) antiobesity compounds, such as fenfluramine, dexfenfluramine, phentermine, sibutramine, orlistat, neuropeptide $Y_1$ or $Y_5$ antagonists, CB1 receptor inverse agonists and antagonists, $β_3$ adrenergic receptor agonists, melanocortin-receptor agonists, in particular melanocortin-4 receptor agonists, ghrelin antagonists, bombesin receptor agonists (such as bombesin receptor subtype-3 agonists), and melanin-concentrating hormone (MCH) receptor antagonists;

(m) ileal bile acid transporter inhibitors;

(n) agents intended for use in inflammatory conditions such as aspirin, non-steroidal anti-inflammatory drugs (NSA/Ds), glucocorticoids, azulfidine, and selective cyclooxygenase-2 (COX-2) inhibitors;

(o) antihypertensive agents, such as ACE inhibitors (enalapril, lisinopril, captopril, quinapril, tandolapril), A-II receptor blockers (losartan, candesartan, irbesartan, valsartan, telmisartan, and eprosartan), beta blockers and calcium channel blockers;

(p) glucokinase activators (GKAs), such as those disclosed in WO 03/015774; WO 04/076420; and WO 04/081001;

(q) inhibitors of 11β-hydroxysteroid dehydrogenase type 1, such as those disclosed in U.S. Pat. No. 6,730,690; WO 03/104207; and WO 04/058741;

(r) inhibitors of cholesteryl ester transfer protein (CETP), such as torcetrapib; and (s) inhibitors of fructose 1,6-bisphosphatase, such as those disclosed in U.S. Pat. Nos. 6,054,587; 6,110,903; 6,284,748; 6,399,782; and 6,489,476.

Dipeptidyl peptidase-IV inhibitors that can be combined with compounds of structural formula I include those disclosed in U.S. Pat. No. 6,699,871; WO 02/076450 (3 Oct. 2002); WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); WO 03/082817 (9 Oct. 2003); WO 03/000181 (3 Jan. 2003); WO 04/007468 (22 Jan. 2004); WO 04/032836 (24 Apr. 2004); WO 04/037169 (6 May 2004); and WO 04/043940 (27 May 2004). Specific DPP-IV inhibitor compounds include isoleucine thiazolidide (P32/98); NVP-DPP-728; vildagliptin (LAF 237); P93/01; and saxagliptin (BMS 477118).

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB 1 receptor antagonists or inverse agonists, melanocortin receptor agonists, in particular, melanocortin-4 receptor agonists, ghrelin antagonists, bombesin receptor agonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); and J. A. Fernandez-Lopez, et al., "Pharmacological Approaches for the Treatment of Obesity," *Drugs*, 62: 915-944 (2002).

Neuropeptide Y5 antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB 1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. No. 5,532,237; U.S. Pat. No. 5,292,736; PCT Publication WO 03/086288; PCT Publication WO 03/087037; PCT Publication WO 04/048317; PCT Publication WO 03/007887; PCT Publication WO 03/063781; PCT Publication WO 03/075660; PCT Publication WO 03/077847; PCT Publication WO 03/082190; PCT Publication WO 03/082191; PCT Publication WO 03/087037; PCT Publication WO 03/086288; PCT Publication WO 04/012671; PCT Publication WO 04/029204; PCT Publication WO 04/040040; PCT Publication WO 01/64632; PCT Publication WO 01/64633; and PCT Publication WO 01/64634.

Melanocortin-4 receptor (MC4R) agonists useful in the present invention include, but are not limited to, those disclosed in U.S. Pat. No. 6,294,534, U.S. Pat. Nos. 6,350,760, 6,376,509, 6,410,548, 6,458,790, U.S. Pat. No. 6,472,398, U.S. Pat. No. 5,837,521, U.S. Pat. No. 6,699,873, which are hereby incorporated by reference in their entirety; in US Patent Application Publication Nos. US 2002/0004512, US2002/0019523, US2002/0137664, US2003/0236262, US2003/0225060, US2003/0092732, US2003/109556, US 2002/0177151, US 2002/187932, US 2003/0113263, which are hereby incorporated by reference in their entirety; and in WO 99/64002, WO 00/74679, WO 02/15909, WO 01/70708, WO 01/70337, WO 01/91752, WO 02/068387, WO 02/068388, WO 02/067869, WO 03/007949, WO 2004/024720, WO 2004/089307, WO 2004/078716, WO 2004/078717, WO 2004/037797, WO 01/58891, WO 02/070511, WO 02/079146, WO 03/009847, WO 03/057671, WO 03/068738, WO 03/092690, WO 02/059095, WO 02/059107, WO 02/059108, WO 02/059117, WO 02/085925, WO 03/004480, WO 03/009850, WO 03/013571, WO 03/031410, WO 03/053927, WO 03/061660, WO 03/066597, WO 03/094918, WO 03/099818, WO 04/037797, WO 04/048345, WO 02/018327, WO 02/080896, WO 02/081443, WO 03/066587, WO 03/066597, WO 03/099818, WO 02/062766, WO 03/000663, WO 03/000666, WO 03/003977, WO 03/040107, WO 03/040117, WO 03/040118, WO 03/013509, WO 03/057671, WO 02/079753, WO 02/092566, WO 03/-093234, WO 03/095474, and WO 03/104761.

The potential utility of safe and effective activators of glucokinase (GKAs) for the treatment of diabetes is discussed in J. Grimsby et al., "Allosteric Activators of Glucokinase: Potential Role in Diabetes Therapy," *Science,* 301: 370-373 (2003).

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Synthetic methods for preparing the compounds of the present invention are illustrated in the following Schemes and Examples. Starting materials are commercially available or may be made according to procedures known in the art or as illustrated herein.

The compounds of the present invention can be prepared, by various modifications, starting from amino heterocyclic intermediates of formula II and α,β-unsaturated nitrile intermediates such as those of the general formula III. The preparation of these intermediates and their conversion to compounds of formula I are described in the following schemes.

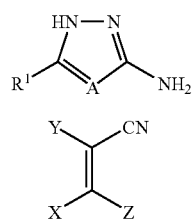

II

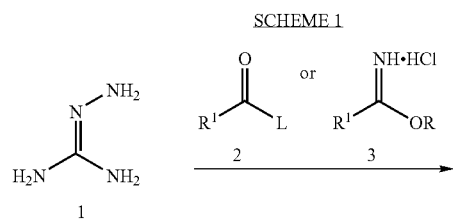

III wherein A, $R^1$, and Z are defined as defined above; Y is CN or $C(S)NH_2$, and X is H or a leaving group.

SCHEME 1

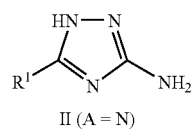

II (A = N)

Compounds of formula II are commercially available, known in the literature, or may be conveniently prepared by a variety of methods familiar to those skilled in the art. One common route to II wherein A is N is illustrated in Scheme 1. Aminoguanidine (1) is reacted with an acid or acid derivative 2, in which L is a leaving group [e.g., $R^1$(CO)L is a carboxylic acid, ester, acid anhydride, or acid chloride] or with an iminoether 3 (R is typically methyl or ethyl) with heating to give the aminotriazole II. Useful references for this transformation include: F. Kurzer and L. E. A. Godfrey, *Angew. Chem.*, 75, 1157 (1963); S. C. Bell, U.S. Pat. No. 4,347,362 (1982); C. A. Lipinski et al., *J. Med. Chem.*, 28, 1628 (1985); V. V. Kiseleva et al., *Izv. Akad. Nauk SSSR, Ser. Khim.*, 2075 (1990); A. A. Abdel-Hafez et al., *Arztzeim.-Forsch.*, 52, 833 (2002); and T. Akbarzadeh et al., *Bioorg. Med. Chem.*, 11, 769 (2003).

SCHEME 2

As illustrated in Scheme 2, aminotriazoles of formula II (A=N) in which $R^1$ is of the formula $R^4O$—, $R^4S$—, or $R^5R^6N$— may be conveniently synthesized by reaction of hydrazine with an appropriate N-cyanoazomethine 4, in which X is a leaving group such as methoxy, ethoxy, or methylthio [B. T. Heitke and C. G. McCarty, *J. Org. Chem.*, 39, 1522 (1974)].

SCHEME 3

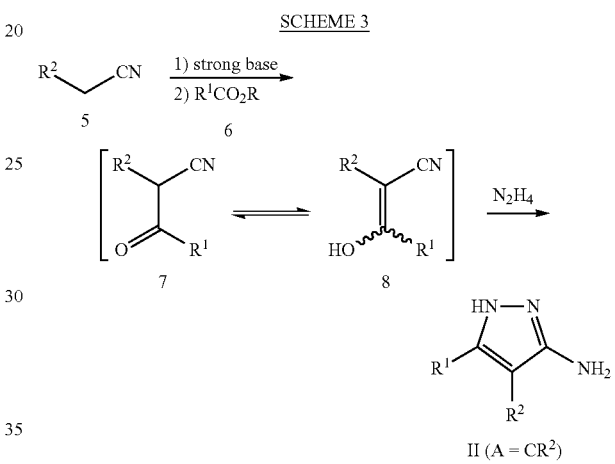

A general route to intermediates of formula II wherein A is $CR^2$ is shown in Scheme 3. A nitrile derivative of structure 5 is treated with a suitable strong base (e.g., potassium tert-butoxide, butyllithium, sodium amide, or sodium hydride) to form the anion and then treated with an ester 6 (or related derivative) to give the acylated product 7, which is in equilibrium with the enol form 8. Subsequent reaction with hydrazine, for example, in ethanol at reflux, affords the aminopyrazole of structure II. Useful references for this transformation include: E. L. Anderson et al., *J. Med. Chem.*, 7, 259 (1964); K. Takahashi et al., *Synthesis*, 794 (1985); E. Lunt et al., *J. Med. Chem.*, 30, 357 (1987); D. Fouque et al., *Synth. Commun.*, 25, 3443 (1995); T. Honma et al., *J. Med. Chem.*, 44, 4628 (2001); N. Sato et al., *J. Med. Chem.*, 46, 666 (2003). Similar syntheses via enol ethers or enamines analogous to 8 are also well known [e.g., H. Baganz et al., *Chem. Ber.*, 98, (1965); E. Alcade et al., *J. Heterocycl. Chem.*, 11, 423 (1974); K. M. Dawood et al., *J. Chem. Res. (S)*, 208 (1998); and V. N. Belov et al., *Eur. J. Org. Chem.*, 551 (2003)].

SCHEME 4

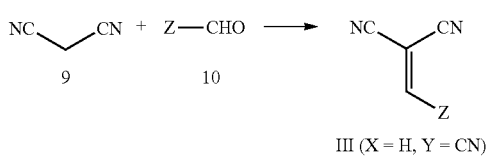

III (X = H, Y = CN)

-continued

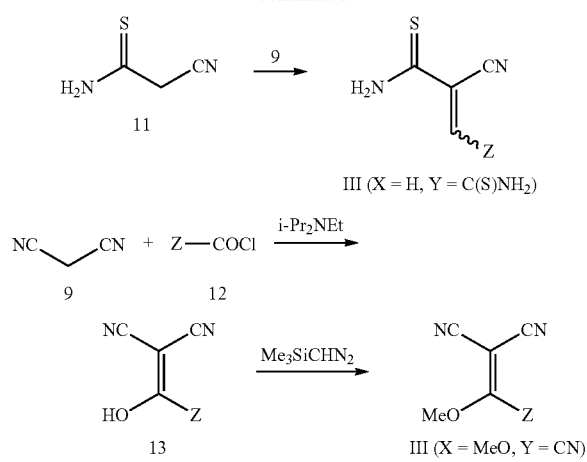

III (X = H, Y = C(S)NH₂)

III (X = MeO, Y = CN)

As shown in Scheme 4, condensation of malononitrile (9) with aldehyde 10, typically run in an alcoholic solvent in the presence of a catalyst such as piperidine, affords intermediate m (X=H, Y=CN) [see, for example: M. Boehringer et al. WO 03/068757 (2003); A. M. Shestapalov et al., Chem. Heterocycl. Compd. (Engl. Transl. of Khim. Geterotsikl. Soedin.), 38, 1345 (2002); A. J. Fatiadi, Synthesis, 165 (1978); R. F. Silver et al., Can. J. Chem., 45, 1001 (1967)]. Similar condensation of 9 with 2-cyanothioacetamide (11) gives III [X=H, Y=C(S)NH₂] [J. S. A. Brunskill and A. De, J. Chem. Soc. Perkin Trans. 1, 629 (1978)]. Reaction of 9 with acid chloride 12 in the presence of a tertiary amine such as N,N-diisopropylethylamine provides adduct 13, which may be methylated with diazomethane or (trimethylsilyl)diazomethane to yield III (X=OMe, Y=CN) [see, for example, G. C. Hirst et al. US 2002/0156081; T. Aoyama et al., Chem. Pharm. Bull., 32, 3759 (1984)]. Analogous III (Y=CN) in which the leaving group X=SMe or NR₂ may also be prepared [see, for example, Y. Tominaga et al., Heterocycles, 26, 613 (1987); Y. Tominaga et al., J. Heterocycl. Chem., 27, 647 (1990)].

SCHEME 5

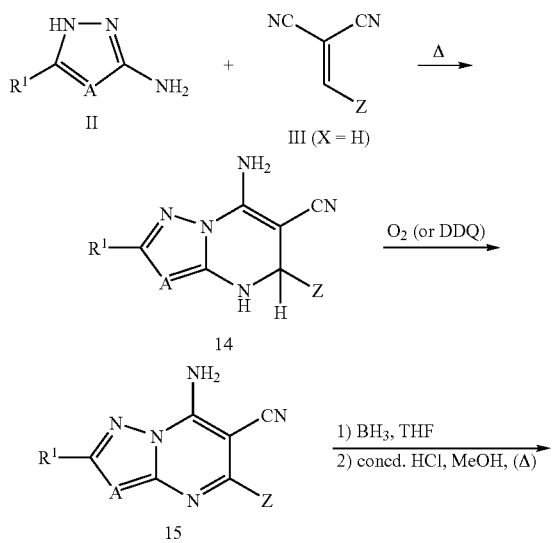

-continued

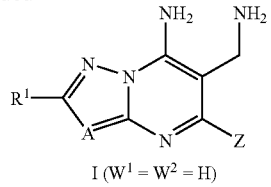

I (W¹ = W² = H)

As shown in Scheme 5, an aminoheterocycle of formula II may be reacted with an α,β-unsaturated nitrile of formula III (X=H, Y=CN) to give initially a fused dihydropyrimidine of structure 14 (or tautomer) [J. J. Vaquero et al., Synthesis, 33 (1987); W. Ried and S. Aboul-Fetouh, Tetrahedron, 44, 7155 (1988)]. Typically this reaction is carried out in a high-boiling solvent such as pyridine or N,N-dimethylformamide at reflux. Usually 14 is not isolated. Instead, on continued heating in air, spontaneous oxidation to the aromatic heterocycle 15 generally occurs [see, for example: A. M. S. Youssef et al., J. Korean Chem. Soc., 45, 448 (2001); A. A. Hassanien et al., J. Chinese Chem. Soc., 47, 1273 (2000); F. M. Abdelrazek, J. Prakt. Chem., 331, 475 (1989); S. A. S. Ghozlan and A. Z. A. Hassanian, Tetrahedron, 58, 9423 (2002); M. H. Elnagdi et al., Collect. Czech. Chem. Commun., 54, 1082 (1989); A. Al-Enzy et al., J. Chem. Res. (M), 116 (1997)]. In some instances where the air oxidation does not proceed satisfactorily, an oxidizing agent such as 2,3-dichloro-5,6-dicyano-1,4-benzoquinone (DDQ) may be added, and the mixture is either stirred at ambient temperature [J. J. Vaquero et al., Synthesis, 33 (1987)] or heated to drive the oxidation to completion. The cyano group of 15 may be reduced to aminomethyl by various methods, depending on the compatibility of functional groups in the molecule. Scheme 5 shows the convenient reduction by borane-tetrahydrofuran complex. The amine may be liberated from the resulting amine-borane complex by treatment with methanol and excess concentrated aqueous hydrochloric acid, with heating as necessary. This yields the product of formula I. Reaction of II with higher oxidation state III (X=OMe, SMe, or NH₂, etc.) under similar conditions may give 15 directly [see, for example: Y. Tominaga et al., Chem. Pharm. Bull., 33, 962 (1985); W. Ried and S. Aboul-Fetouh, Tetrahedron, 44, 7155 (1988); A. G. A. Elagamey and F. M. A.-A. El-Taweel, J. Prakt. Chem., 333, 333 (1991)]. In most cases, however, superior yields of 15 where Z is aryl or heteroaryl are obtained by use of III (X=H) as shown in Scheme 5. Also, 2-cyanothioacetamide-derived III [X=H, Y=C(S)NH₂] has been used in place of malononitrile-derived III (X=H, Y=CN) to obtain intermediates of general structure 15 [S. M. Hussain et al., Tetrahedron, 44, 241 (1988); S. M. Hussain et al., Indian J. Chem., 27B, 421 (1988).

It should be noted that condensation of II with III may give more than one regioisomeric product and that 15 may not always be the major isomer. In reactions of this type, aspects of regioisomerism and spectral methods for structure assignments have been discussed in the literature [see, for example: A. M. S. Youssef et al., J. Korean Chem. Soc., 45, 448 (2001); A. A. Hassanien et al., J. Chinese Chem. Soc., 47, 1273 (2000); M. H. Elnagdi et al., Collect. Czech. Chem. Commun., 54, 1082 (1989)]. Furthermore, in the case of aminotriazole starting materials of formula II, any 1,2,4-triazolo[4,3-a]pyrimidine isomer that forms during the condensation reaction may rearrange to the generally more stable 1,2,4-triazolo[1,5-a]pyrimidine isomer (i.e., formula I, A=N) during the acidic work-up of the subsequent borane reduction. Such rearrangements are well documented in the literature [D. J. Brown and T. Nagamatsu, Aust. J. Chem., 30, 2515 (1977); H. S. El Khadem et al., Heterocycles, 28, 239 (1989)].

SCHEME 6

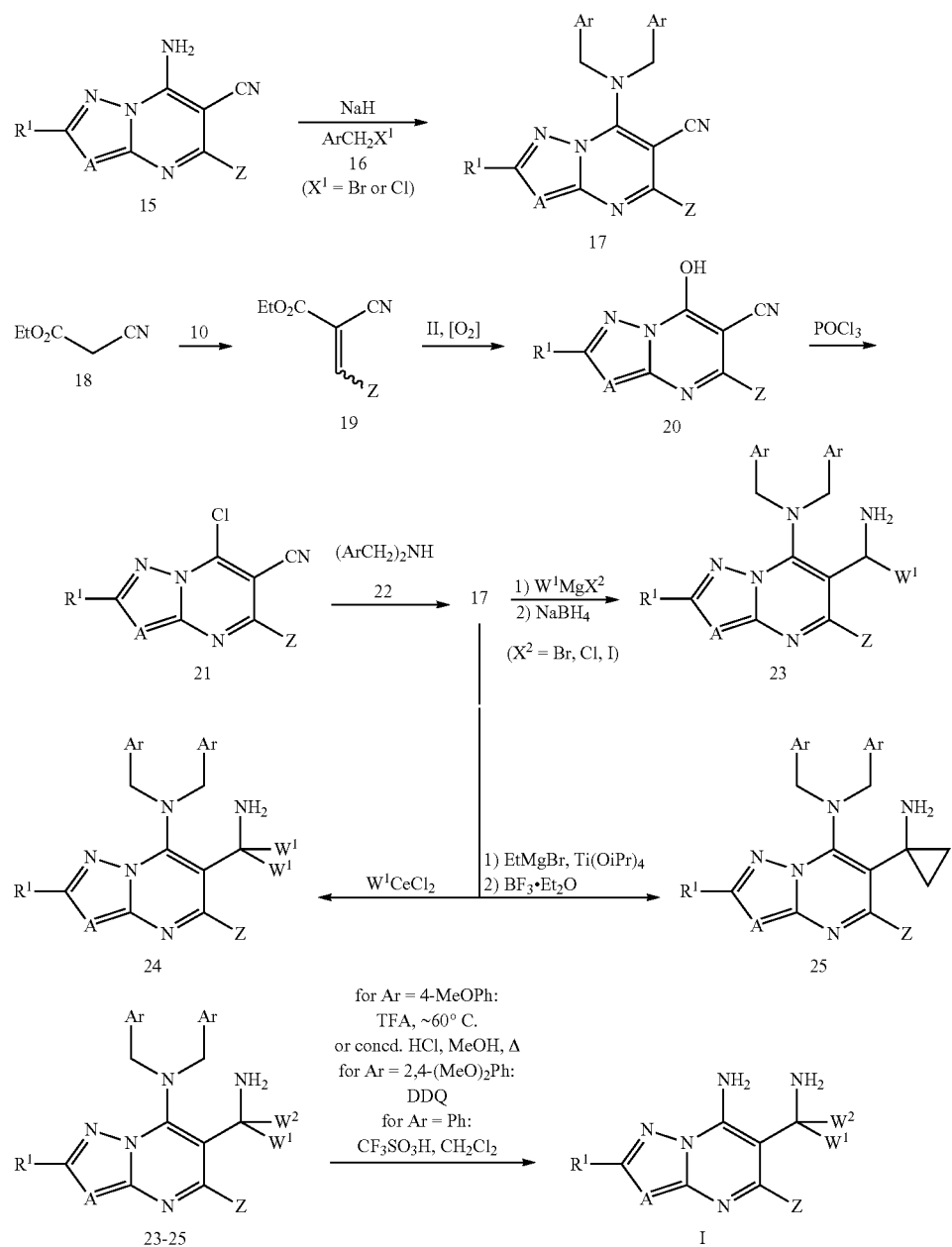

Scheme 6 illustrates some representative but non-limiting methods for the synthesis of compounds of formula I wherein $W^1$ and/or $W^2$=$C_{1-4}$ alkyl. It is first advantageous to fully protect the primary amino group of 15. This may be accomplished by treating 15 with sodium hydride and an excess of arylmethyl halide 16 (e.g., 4-methoxybenzyl chloride or benzyl bromide) in an anhydrous polar solvent such as dimethyl sulfoxide or N,N-dimethylformamide [for analogous alkylation, see S. Kataoka et al., *Chem. Pharm. Bull.*, 38, 3147 (1990); G. B. Evans et al., *J. Org. Chem.*, 69, 2217 (2004)]. Alternatively, 17 may be prepared by a different route in which the amino group is introduced in a protected form. Thus, ethyl cyanoacetate is condensed with aldehyde 10 under conditions similar to those in Scheme 4 to give the adduct 19. In analogy to the synthesis of 15 from II and III (X=H) as in Scheme 5, 19 can be condensed with an amino heterocycle of formula II in the presence of air to afford the fused pyrimidinol 20 [see, for example: M. H. Elnagdi et al., *Collect. Czech. Chem. Commun.*, 54, 1082 (1989); F. M. Abdelrazek, *J. Prakt. Chem.*, 331, 475 (1989); F. M. Abdelrazek et al., *Egypt. J. Chem.*, 42, 75 (1999); A. A. Hassanien et al., *J. Chinese Chem. Soc.*, 47, 1273 (2000)]. Treatment of 20 with phosphorus oxychloride (usually at elevated temperature and optionally in the presence of a tertiary amine such as N,N-dimethylaniline) affords the chloro heterocycle 21 [see, for example, reports of analogous preparations: W. A. Kleshick and J. Bordner, *J. Heterocycl. Chem.*, 26, 1489 (1989); Y. Tominaga et al., *Chem. Pharm. Bull.*, 33, 962 (1985); T. Novinson et al., *J. Med. Chem.*, 25, 420 (1982); J. S. Bajwa and P. J. Sykes, *J. Chem. Soc. Perkin Trans* 1, 3085 (1979)].

Subsequent displacement of the chloro group of 21 by the bis(arylmethyl)amine 22 [e.g., bis(4-methoxybenzyl)amine, bis(2,4-dimethoxybenzylamine) or dibenzylamine)] yields 17 [for similar reactions, see: V. Mesguiche et al., *Bioorg. Med. Chem. Lett.*, 13, 217 (2003); M. J. Krische et al., *Helv. Chim. Acta*, 81, 1921 (1998); G. Berecz et al., *J. Heterocycl. Chem.*, 39, 703 (2002); Y. Tominaga et al., *Chem. Pharm. Bull.*, 33, 962 (1985); T. Novinson et al., *J. Med. Chem.*, 25, 420 (1982)]. Addition of a Grignard reagent $W^1$MgBr, $W^1$MgCl, or $W^1$MgI to the nitrile group of 17 followed by reduction of the intermediate imine with sodium borohydride in methanol [E. Leclerc et al., *J. Org. Chem.*, 67, 8928 (2002)] provides the amine 23 bearing a monoalkyl substituent at the adjacent carbon. Reaction of 17 with three equivalents of an alkylcerium dichloride $W^1$CeCl$_2$ [prepared in situ by low temperature addition of an alkyllithium $W^1$Li (e.g., methyllithium) to dry cerium(III) chloride] provides the gem-disubstituted derivative 24 [for similar examples, see: E. Ciganek, *J. Org. Chem.*, 57, 4521 (1992); V. Fedij et al., *Tetrahedron: Asymmetry*, 5, 1131 (1994); V. Fedij et al., U.S. Pat. No. 5,347,017 (1994)]. Also, reaction of 17 with ethylmagnesium bromide in the presence of titanium tetraisopropoxide followed by treatment with boron trifluoride etherate [P. Bertus and J. Szymoniak, *J. Org. Chem.*, 67, 3965 (2002); P. Bertus and J. Szymoniak, *Synlett.*, 265 (2003)] affords the 1-aminocyclopropyl derivative 25. A related synthesis of 1-aminocyclopropyl derivatives using diethylzinc [S. Wiedemann et al., *Org. Lett.*, 5, 753 (2003)] may also be employed. Finally, the intermediates 23-25 are deprotected to yield the compounds of formula I. Some analogous deprotections have been carried out with (1) trifluoroacetic acid at 60° C. [for Ar=4-methoxyphenyl: V. Mesguiche et al., *Bioorg. Med. Chem. Lett.*, 13, 217 (2003)], (2) a mixture of concentrated hydrochloric acid and methanol at reflux [for Ar=4-methoxyphenyl: G. B. Evans et al., *J. Med. Chem.*, 46, 5271 (2003)], (3) 2,3-dichloro-5,6-dicyano-1,4-benzoquinone (DDQ) [for Ar=2,4-dimethoxyphenyl: M. J. Krische et al., *Helv. Chim. Acta*, 81, 1921 (1998)], or (4) trifluoromethanesulfonic acid in dichloromethane at 40° C. [for Ar=phenyl: D. L. Boger et al., *J. Org. Chem.*, 57, 4333 (1992)].

The amine of formula I is purified from unwanted side products, if necessary, by recrystallization, trituration, preparative thin layer chromatography, flash chromatography on silica gel as described by W. C. Still et al, *J. Org. Chem.*, 43, 2923 (1978), or HPLC. Compounds which are purified by HPLC may be isolated as the corresponding salt. Purification of intermediates is achieved in the same manner.

In some cases the intermediates or final products may be further modified, for example, by manipulation of $R^1$ and/or $R^2$ substituents. These manipulations may include, but are not limited to, reduction, oxidation, alkylation, acylation, and hydrolysis reactions which are commonly known to those skilled in the art. Examples of a few of these transformations are illustrated in Schemes 7 and 8 below.

SCHEME 7

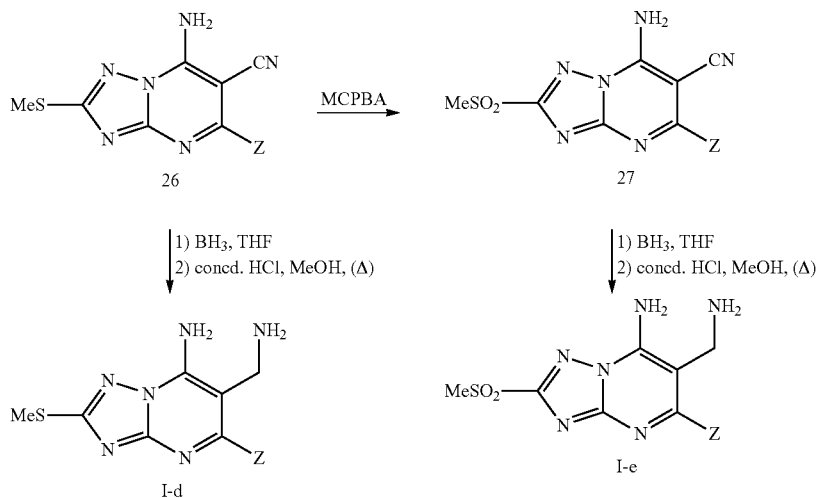

One example of functional group transformations is shown in Scheme 7. Thus, the methylthio substituent of 26 may be oxidized to the corresponding sulfone 27 by m-chloroperoxybenzoic acid. Intermediates 26 and 27 may then be individually reduced, as in Scheme 5, to the target compounds I-c and I-d, respectively.

SCHEME 8

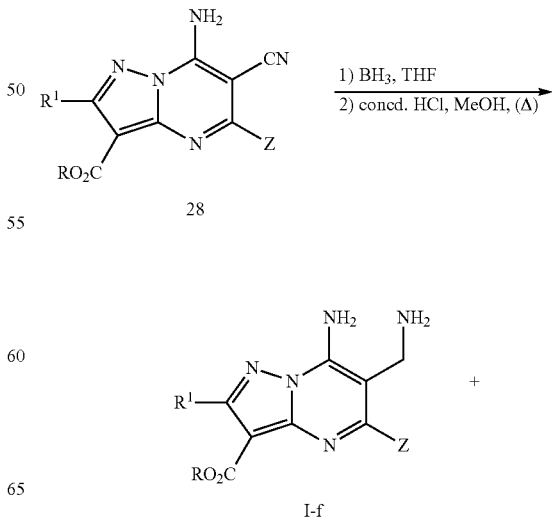

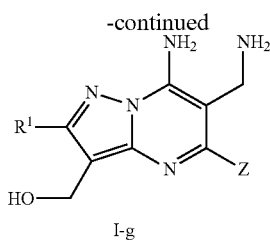

I-g

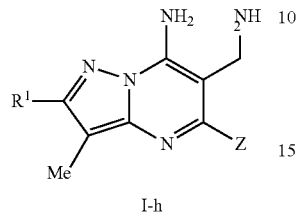

I-h

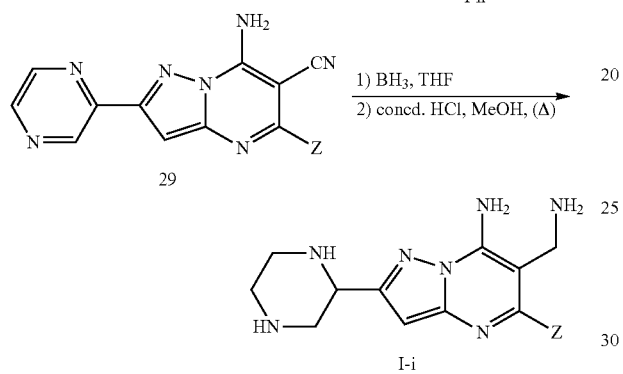

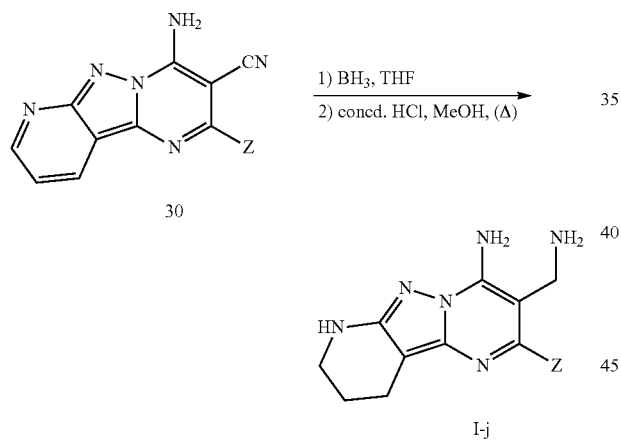

I-j

Scheme 8 shows how some substituent functional groups may be further transformed during the reduction of the nitrile. Thus, 28, which contains an ester substituent on the pyrazolo moiety, may yield multiple products from the borane reduction, including unchanged ester I-e, hydroxymethyl I-f, and methyl I-g. Similarly, the attached pyrazine ring of 29 and the fused pyridine ring of 30 may be reduced at the same time as the nitrile to yield I-h and I-i, respectively.

Various additional functional group manipulations may be carried out, and these will be known to persons skilled in the art.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

(2,4-Dichlorobenzylidene)malononitrile

This material was prepared from malononitrile and 2,4-dichlorobenzaldehyde according to the procedure of M. Boehringer et al., WO 03/068748.

INTERMEDIATE 2

(2,4-Dimethylbenzylidene)malononitrile

This material was prepared from malononitrile and 2,4-dimethylbenzaldehyde according to the procedure of M. Boehringer et al., WO 03/068748.

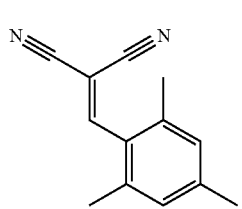

INTERMEDIATE 3

(Mesitylmethylene)malononitrile

In analogy to the methods described by M. Boehringer et al., WO 03/068748, a solution of 25 g (169 mmol) of mesitaldehyde (2,4,6-trimethylbenzaldehyde) and 13.5 g (204 mmol) of malononitrile in 70 mL of n-butanol was stirred at room temperature for 1 h and then treated dropwise with 0.4 mL of piperidine, resulting in a color change and precipitation. After 5 h, the mixture was cooled in a freezer (−20° C.) for 10 min and then filtered. The solid was washed three times with cold n-butanol and then dried to give the title compound as a white solid. LC-MS 197 (M+1). This material has been reported as being made by a similar procedure [A. M. Shestapalov et al., *Chem. Heterocycl. Compd.* (Engl. Transl. of *Khim. Geterotsikl. Soedin.*), 38, 1345 (2002)].

INTERMEDIATE 4

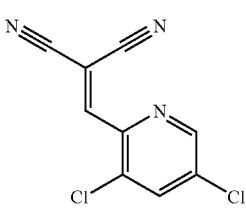

[(3,5-Dichloropyridin-2-yl)methylene]malononitrile

By the method used for Intermediate 3,3,5-dichloropyridine-2-carbaldehyde (R. Bonjouklian et al., WO 02/081482) and malononitrile were reacted to give the title compound as a dark greenish powder. LC-MS 224 (M+1).

INTERMEDIATE 5

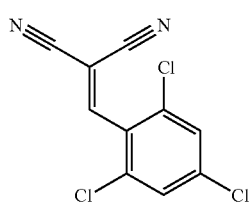

(2,4,6-Trichlorobenzylidene)malononitrile

By the method used for Intermediate 3,2,4,6-trichlorobenzaldehyde [S. Banfi et al., *J. Chem. Soc. Perkin Trans.* 2, 871 (2000)] and malononitrile were reacted to give the title compound as a pinkish solid. LC-MS 257 (M+1).

INTERMEDIATE 6

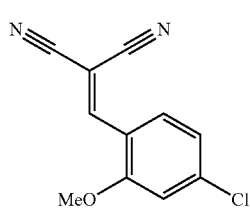

(4-Chloro-2-methoxybenzylidene)malononitrile

Step A

4-Chloro-2-methoxybenzaldehyde

Following the general method of R. A. Miller and R. S. Hoerrner, *Org. Lett.*, 5, 285 (2003), a solution of 2.5 g (14.1 mmol based on 97% purity) of 4-chloro-2-methoxybenzyl alcohol in 35 mL of toluene was treated with 35 mL of water and 3.54 g (42.3 mmol) of sodium bicarbonate. The resulting two-phase mixture was stirred at ambient temperature as 7.2 g (28.2 mmol) of iodine was added, followed by 0.223 g (1.41 mmol) of 2,2,6,6-tetramethyl-1-piperidinyloxy, free radical (TEMPO). After 3 days, the dark mixture was cooled to 5° C. and quenched by addition of a solution of 1.8 g of sodium sulfite in 18 mL of water. The mixture was partitioned between ethyl acetate and water. The organic layer was washed with saturated aqueous sodium bicarbonate solution and then with brine. The organic phase was then dried over anhydrous sodium sulfate. The supernatant was concentrated to a volume of approximately 5 mL and kept at 5° C. for 1 h. The solid that separated was collected on a filter, washed twice with small volumes of cold toluene, and dried in vacuo to yield the title compound as a white solid. LC-MS 171 (M+1).

Step B (4-Chloro-2-methoxybenzylidene)malononitrile

By the method used for Intermediate 3,4-chloro-2-methoxybenzaldehyde from Step A was reacted with malononitrile to afford the title compound as a yellow solid. LC-MS 219 (M+1).

Additional substituted benzylidenemalononitrile derivatives (Table 1) were prepared by the procedures described above for Intermediates 1-6.

TABLE 1

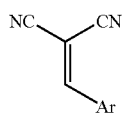

| Intermediate | Ar | Mass Spectrum (M + 1) |
|---|---|---|
| 7 | 2-F-4-Cl—Ph | 207 |
| 8 | 2-Me-4-Cl—Ph | 203 |
| 9 | 2-F-4-CF$_3$—Ph | 241 |
| 10 | 2,3-F$_2$-4-Me—Ph | 205 |
| 11 | 2,4,5-F$_3$—Ph | 209 |
| 12 | 2,4-Cl$_2$-6-MeO—Ph | 253 |

INTERMEDIATE 13

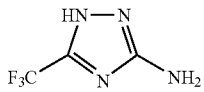

5-(Trifluoromethyl)-1H-1,2,4-triazol-3-amine

The title compound was prepared by the procedure of V. A. Lopyrev and T. N. Rakbmatulina, *J. Gen. Chem. USSR* (Engl. Transl. of *Zh. Obshch. Khim.*), 53, 1684 (1983).

INTERMEDIATE 14

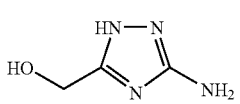

(3-Amino-1H-1,2,4-triazol-5-yl)methanol

The title compound was prepared by the procedure of N. Bru-Mahniez et al., U.S. Pat. No. 5,387,747 (1995).

INTERMEDIATE 15

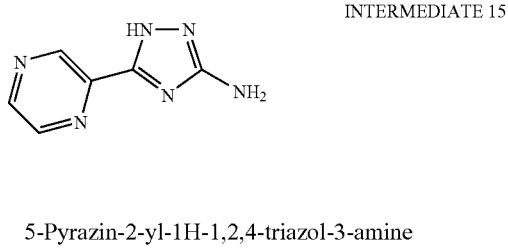

5-Pyrazin-2-yl-1H-1,2,4-triazol-3-amine

The title compound was prepared by the general method of H. L. Yale and J. J. Piala, *J. Med. Chem.*, 9, 42 (1966).

INTERMEDIATE 16

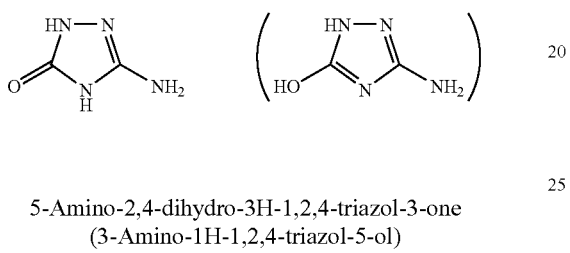

5-Amino-2,4-dihydro-3H-1,2,4-triazol-3-one
(3-Amino-1H-1,2,4-triazol-5-ol)

The title compound was prepared according to the procedure of L. E. A. Godfrey and F. Kurzer, *J. Chem. Soc.*, 3437 (1960).

INTERMEDIATE 17

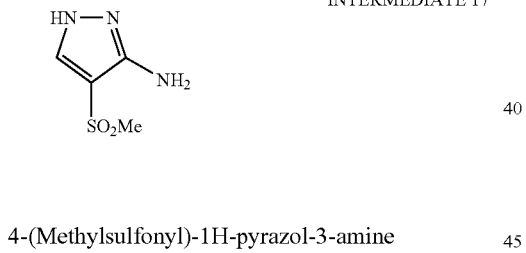

4-(Methylsulfonyl)-1H-pyrazol-3-amine

The title compound was prepared by the procedure of E. Lunt et al., *J. Med. Chem.*, 30, 357 (1987).

INTERMEDIATE 18

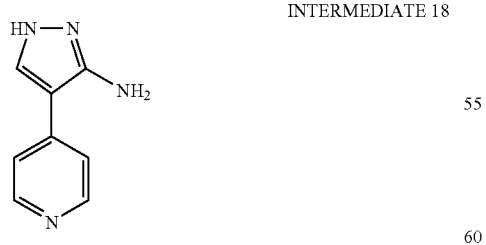

4-Pyridin-4-yl-1H-pyrazol-3-amine

The title compound was prepared by the procedure of M. E. Fraley et al., *Bioorg. Med. Chem. Lett.*, 12, 2767 (2002).

INTERMEDIATE 19

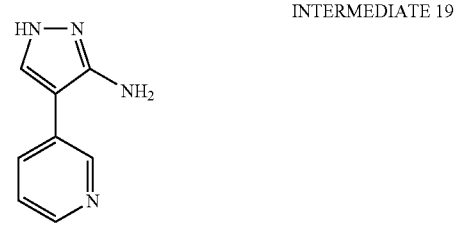

4-Pyridin-3-yl-1H-pyrazol-3-amine

The title compound was prepared by the procedure of M. E. Fraley et al., *Bioorg. Med. Chem. Lett.*, 12, 2767 (2002).

INTERMEDIATE 20

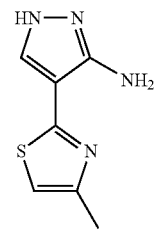

4-Pyridin-2-yl-1H-pyrazol-3-amine

The title compound was prepared by the procedure of M. E. Fraley et al., *Bioorg. Med. Chem. Lett.*, 12, 2767 (2002).

INTERMEDIATE 21

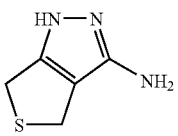

4-(4-Methyl-1,3-thiazol-2-yl)-1H-pyrazol-3-amine

The title compound was prepared in analogy to Intermediates 18-20 by the method of M. E. Fraley et al., *Bioorg. Med. Chem. Lett.*, 12, 2767 (2002).

INTERMEDIATE 22

4,6-Dihydro-1H-thieno[3,4-c]pyrazol-3-amine

To a suspension of 1.00 g (7.86 mmol) of 4-cyanotetrahydrothiophenone in 6 mL of ethanol was added 0.275 mL (286 mg, 4.76 mmol) of glacial acetic acid, followed by 0.475 mL (489 mg, 9.77 mmol) of hydrazine hydrate. The resulting clear solution was stirred overnight under nitrogen with heating in an oil bath at 80° C. The cooled reaction mixture was then partitioned between ethyl acetate and saturated sodium bicarbonate aqueous solution. The aqueous phase was re-extracted with an additional portion of ethyl acetate. The combined organic fractions were washed with saturated sodium chloride aqueous solution, then dried over anhydrous sodium sulfate, filtered, and concentrated to a syrup. Trituration of this oil with dichloromethane containing a small amount (less than 3%) of methanol resulted in crystallization. The suspension was heated to gentle reflux for a few minutes and then cooled. The solid was collected on a filter and washed with a small volume of dichloromethane to yield the title compound as almost colorless crystals. LC-MS 142 (M+1).

INTERMEDIATE 23

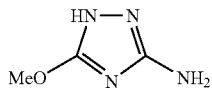

5-Methoxy-1H-1,2,4-triazol-3-amine

The title compound was prepared according to the procedure of B. T. Heitke and C. G. McCarty, *J. Org. Chem.*, 39, 1522 (1974).

INTERMEDIATE 24

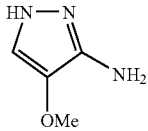

4-Methoxy-1H-pyrazol-3-amine

The title compound was prepared according to the procedure of T. Okazaki et al., U.S. Pat. No. 5,475,114 (1995).

Example 1

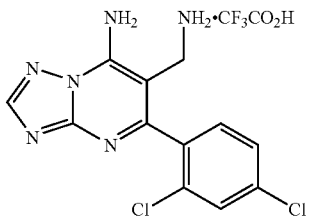

6-(Aminomethyl)-5-(2,4-dichlorophenyl)[1,2,4]triazolo[1,5-a]pyrimidin-7-amine, Trifluoroacetic Acid Salt Step A 7-Amino-5-(2,4-dichlorophenyl)[1,2,4]triazolo[1,5-a]pyrimidine-6-carbonitrile A solution of 157 mg (1.87 mmol) of 3-amino-1,2,4-triazole and 417 mg (1.87 mmol) of (2,4-dichlorobenzylidene) malononitrile (Intermediate 1) in 4.7 mL of anhydrous pyridine was stirred at reflux under air for 22 h and then cooled and concentrated in vacuo. The residue was partitioned between 5% aqueous citric acid solution and a 1:1 mixture of ethyl acetate and tetrahydrofuran. The organic phase was washed once more with the citric acid solution and then (after addition of some more tetrahydrofuran) with saturated aqueous sodium chloride solution. The combined aqueous fractions were re-extracted with a 2:3 mixture of ethyl acetate and tetrahydrofuran. The combined organics were dried over magnesium sulfate, filtered, and concentrated in vacuo. Purification of the residue by flash chromatography on silica gel (gradient elution with 2-3% methanol in dichloromethane) afforded the title compound as an amber-colored glass, which was used without further purification. LC-MS 305 (M+1).

Step B 6-(Aminomethyl)-5-(2,4-dichlorophenyl)[1,2,4]triazolo[1,5-a]pyrimidine-7-amine, Trifluoroacetic Acid Salt A solution of 73.2 mg (0.24 mmol) of 7-amino-5-(2,4-dichlorophenyl)[1,2,4]triazolo[1,5-a]pyrimidine-6-carbonitrile from Step A in 1.2 mL of anhydrous tetrahydrofuran was stirred under nitrogen at ambient temperature as 1.2 mL (1.2 mmol) of 1M borane-tetrahydrofuran complex in tetrahydrofuran was added dropwise by syringe over about 10 min. After 7 h, the mixture was quenched by cautious dropwise addition of 0.36 mL (4.32 mmol) of concentrated hydrochloric acid (gas evolution) followed by addition of 1.2 mL of methanol. After being stirred overnight at ambient temperature, the solution was transferred to a sealed tube and stirred with heating in an oil bath at 80° C. for 6 h. The solution was then evaporated to dryness. Purification of the residue by preparative HPLC (C18 reverse phase column, gradient elution with 2-75% acetonitrile in water containing 0.05% trifluoroacetic acid) yielded the title compound as a glass. LC-MS 309 (M+1).

Example 2

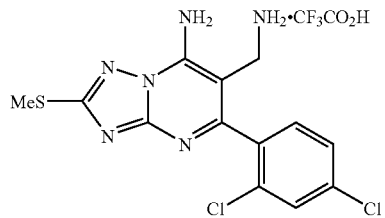

6-(Aminomethyl)-5-(2,4-dichlorophenyl)-2-(methylthio)[1,2,4]triazolo[1,5-a]pyrimidin-7-amine, Trifluoroacetic Acid Salt Step A 7-Amino-5-(2,4-dichlorophenyl)-2-(methylthio)[1,2,4]triazolo[1,5-a]pyrimidine-6-carbonitrile According to the procedure of Example 1, Step A, commercial 5-(methylthio)-1H-1,2,4-triazol-3-amine and (2,4- dichlorobenzylidene)malononitrile (Intermediate 1) were reacted to give the title compound as a dark brown solid. LC-MS 351 (M+1).

Step B

6-(Aminomethyl)-5-(2,4-dichlorophenyl)-2-(methylthio)[1,2,4]triazolo[1,5-a]pyrimidin-7-amine Trifluoroacetic Acid Salt Essentially by the procedure of Example 1, Step B, 7-amino-5-(2,4-dichlorophenyl)-2-(methylthio)[1,2,4]triazolo[1,5-a]pyrimidine-6-carbonitrile from Step A was converted to the title compound as a yellow solid. LC-MS 355 (M+1).

Example 3

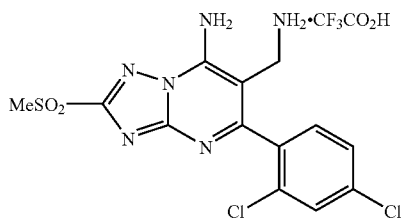

6-(Aminomethyl)-5-(2,4-dichlorophenyl)-2-(methylsulfonyl)[1,2,4]-triazolo[1,5-a]pyrimidin-7-amine, Trifluoroacetic Acid Salt

Step A

7-Amino-5-(2,4-dichlorophenyl)-2-(methylsulfonyl)[1,2,4]triazolo[1,5-a]pyrimidine-6-carbonitrile A mixture of 36 mg (0.103 mmol) of 7-amino-5-(2,4-dichlorophenyl)-2-(methylthio)[1,2,4]triazolo[1,5-a]pyrimidine-6-carbonitrile from Example 2, Step A, 56 mg (0.25 mmol based on 77% purity) of 3-chloroperoxybenzoic acid, and 2 mL of dichloromethane was stirred at ambient temperature for 6.5 h. The solution was concentrated, and the residue was purified by preparative thin-layer chromatography on silica gel (developed in 95:5 dichloromethane:methanol) to give the title compound as a yellow solid. LC-MS 383 (M+1).

Step B

6-(Aminomethyl)-5-(2,4-dichlorophenyl)-2-(methylsulfonyl)[1,2,4]triazolo[1,5-a]pyrimidin-7-amine Trifluoroacetic Acid Salt The title compound was obtained by reduction of 7-amino-5-(2,4-dichlorophenyl)-2-(methylsulfonyl)[1,2,4]triazolo[1,5-a]pyrimidine-6-carbonitrile from Step A, essentially by the procedure of Example 1, Step B, except that the borane reduction was conducted under sonication in an ultrasound bath at ambient temperature. LC-MS 387 (M+1).

Example 4

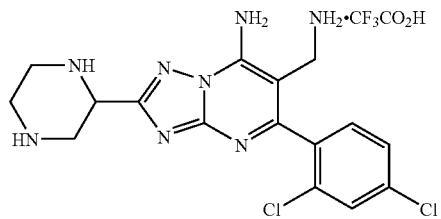

6-(Aminomethyl)-5-(2,4-dichlorophenyl)-2-piperazin-2-yl[1,2,4]triazolo[1,5-a]pyrimidin-7-amine, Trifluoroacetic Acid Salt

Step A

7-Amino-5-(2,4-dichlorophenyl)-2-pyrazin-2-yl[1,2,4]triazolo[1,5-a]pyrimidine-6-carbonitrile In analogy to the procedure of Example 1, Step A (but using gradient elution with 5-10% methanol in dichloromethane for purification), 5-pyrazin-2-yl-1H-1,2,4-triazol-3-amine (Intermediate 15) and (2,4-dichlorobenzylidene)malononitrile (Intermediate 1) were reacted to give the title compound as a dark reddish-orange solid. LC-MS 383 (M+1).

Step B

6-(Aminomethyl)-5-(2,4-dichlorophenyl)-2-piperazin-2-yl[1,2,4]triazolo[1,5-a]pyrimidin-7-amine Trifluoroacetic Acid Salt Borane reduction of 7-amino-5-(2,4-dichlorophenyl)-2-pyrazin-2-yl[1,2,4]triazolo[1,5-a]pyrimidine-6-carbonitrile from Step A according to the method of Example 3, Step B, afforded the title compound as a pale yellow solid. LC-MS 393 (M+1).

Example 5

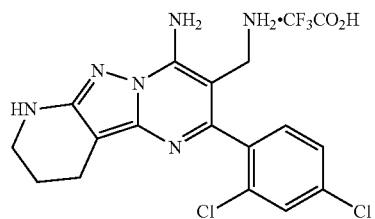

3-(Aminomethyl)-2-(2,4-dichlorophenyl)-7,8,9,10-tetrahydropyrido[2',3':3,4]pyrazolo[1,5-a]pyrimidin-4-amine, Trifluoroacetic Acid Salt

Step A

4-amino-2-(2,4-dichlorophenyl)pyrido[2',3':3,4]pyrazolo[1,5-a]pyrimidine-3-carbonitrile Commercial 1H-pyrazolo[3,4-b]pyridin-3-amine and (2,4-dichlorobenzylidene)malononitrile (Intermediate 1)

were reacted according to the procedure of Example 1, Step A, and the crude product was purified by preparative HPLC (C18 reverse phase column, gradient elution with 10-80% acetonitrile in water containing 0.05% trifluoroacetic acid) to give the title compound as a yellow solid. LC-MS 355 (M+1).

Step B 3-(Aminomethyl)-2-(2,4-dichlorophenyl)-7,8,9,10-tetrahydropyrido-[2',3':3,4]pyrazolo[1,5-a]pyrimidin-4-amine, Trifluoroacetic Acid Salt Borane reduction of 4-amino-2-(2,4-dichlorophenyl)pyrido[2',3':3,4]pyrazolo[1,5-a]pyrimidine-3-carbonitrile from Step A according to the method of Example 3, Step B, afforded the title compound. LC-MS 363 (M+1).

Example 6

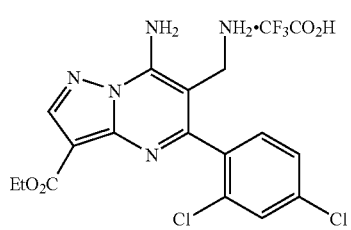

Ethyl 7-amino-6-(aminomethyl)-5-(2,4-dichlorophenyl)pyrazolo[1,5-a]pyrimidine-3-carboxylate, Trifluoroacetic Acid Salt Step A Ethyl 7-amino-6-cyano-5-(2,4-dichlorophenyl)pyrazolo[1,5-a]pyrimidine-3-carboxylate Commercial 3-amino-4-carbethoxypyrazole and (2,4-dichlorobenzylidene)malononitrile (Intermediate 1) were reacted according to the procedure of Example 1, Step A, and the crude product was purified by preparative HPLC(C18 reverse phase column, gradient elution with 30-80% acetonitrile in water containing 0.05% trifluoroacetic acid) to give the title compound as a reddish-orange solid. LC-MS 376 (M+1).

Step B

Ethyl 7-amino-6-(aminomethyl)-5-(2,4-dichlorophenyl)pyrazolo[1,5-a]pyrimidine-3-carboxylate, Trifluoroacetic Acid Salt Borane reduction of ethyl 7-amino-6-cyano-5-(2,4-dichlorophenyl)pyrazolo[1,5-a]pyrimidine-3-carboxylate from Step A according to the procedure of Example 1, Step B, yielded [after separation from a by-product (see Example 7)] the title compound as a pale yellow solid. LC-MS 380 (M+1).

Example 7

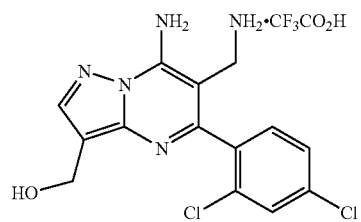

[7-Amino-6-(aminomethyl)-5-(2,4-dichlorophenyl)pyrazolo[1,5-a]pyrimidin-3-yl]methanol Trifluoroacetic Acid Salt Borane reduction of ethyl 7-amino-6-cyano-5-(2,4-dichlorophenyl)pyrazolo[1,5-a]pyrimidine-3-carboxylate from Example 6, Step A, according to the procedure of Example 1, Step B, yielded [after separation from a by-product (see Example 6)] the title compound as a pale yellow solid. LC-MS 338 (M+1).

Example 8

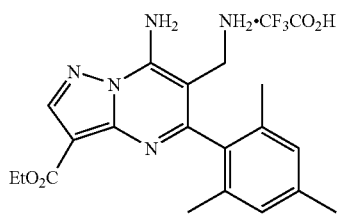

Ethyl 7-amino-6-(aminomethyl)-5-mesitylpyrazolo[1,5-a]pyrimidine-3-carboxylate, Trifluoroacetic Acid Salt Step A Ethyl 7-amino-6-cyano-5-mesitylpyrazolo[1,5-a]pyrimidine-3-carboxylate A solution of 155 mg (1 mmol) of 3-amino-4-carbethoxypyrazole and 196 mg (1 mmol) of (mesitylmethylene)malononitrile (Intermediate 3) in 3 mL of anhydrous pyridine was stirred at reflux under air for 3 days and then cooled and concentrated in vacuo. Because LC-MS indicated the presence of considerable dihydro intermediate, 112 mg (0.49 mmol) of 2,3-dichloro-5,6-cyano-1,4-benzoquinone (DDQ) and 3 mL of isopropanol were added to the residue, and the mixture was stirred at ambient temperature for 1 h. The mixture was concentrated in vacuo, and the residue was purified by flash chromatography on silica gel (elution with 2% methanol in dichloromethane) to give the title compound as an orange solid. LC-MS 350 (M+1).

Step B

Ethyl 7-amino-6-(aminomethyl)-5-mesitylpyrazolo[1,5-a]pyrimidine-3-carboxylate, Trifluoroacetic Acid Salt Borane reduction of ethyl 7-amino-6-cyano-5-mesitylpyrazolo[1,5-a]pyrimidine-3-carboxylate from Step A according to the procedure of Example 1, Step B, yielded (after separation from a by-product corresponding to Example 9) the title compound as a brownish solid. LC-MS 354 (M+1).

Example 9

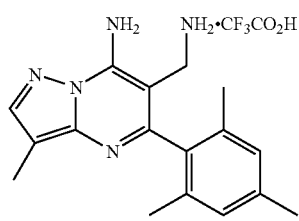

6-(Aminomethyl)-5-mesityl-3-methylpyrazolo[1,5-a]pyrimidin-7-amine, Trifluoroacetic Acid Salt

Step A

Ethyl 7-amino-6-cyano-5-mesitylpyrazolo[1,5-a]pyrimidine-3-carboxylate

In a variation of Example 8, Step A, a solution of 5.69 g (36.7 mmol) of 3-amino-4-carbethoxypyrazole and 6.00 g (30.6 mmol) of (mesitylmethylene)malononitrile (Intermediate 3) in 34 mL of anhydrous pyridine was stirred at reflux under air for 6 days. The dark solution was cooled and concentrated in vacuo. The residue was flash chromatographed on silica gel (gradient elution with 20-50% ethyl acetate in hexane) to give the crude product as a dark solid contaminated with another regioisomer. This material was dissolved in diethyl ether containing a little ethyl acetate. Addition of hexane precipitated a dark, tacky solid. This semisolid was collected and redissolved in 9:1 dichloromethane:methanol. Addition of hexane resulted in precipitation. The precipitate was collected on a filter and dried to give the title compound as a yellow solid. LC-MS 350 (M+1).

Step B 6-(Aminomethyl)-5-mesityl-3-methylpyrazolo[1,5-a]pyrimidin-7-amine, Trifluoroacetic Acid Salt A solution of 1.05 g (3 mmol) of ethyl 7-amino-6-cyano-5-mesitylpyrazolo[1,5-a]pyrimidine-3-carboxylate from Step A in 12 mL of anhydrous tetrahydrofuran was stirred under nitrogen at ambient temperature as 12 mL (12 mmol) of 1M borane-tetrahydrofuran complex in tetrahydrofuran was added gradually by syringe. The mixture was stirred overnight with sonication in an ultrasound bath. Next, the mixture was quenched by cautious gradual addition of approximately 3.6 mL (43 mmol) of concentrated hydrochloric acid (gas evolution) followed by addition of about 50 mL of methanol. The resulting solution was stirred at reflux for 2 h and then evaporated to dryness. Purification of the residual foam by preparative HPLC(C18 reverse phase column, gradient elution with 5-37% acetonitrile in water containing 0.05% trifluoroacetic acid) yielded the title compound as a white solid. LC-MS 296 (M+1).

Example 10

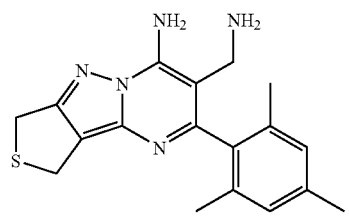

3-(Aminomethyl)-2-mesityl-7H,9H-thieno[3',4':3,4]pyrazolo[1,5-a]pyrimidin-4-amine

Step A

4-Amino-2-mesityl-7H,9H-thieno[3',4':3,4]pyrazolo[1,5-a]pyrimidine-3-carbonitrile A solution of 284 mg (2.01 mmol) of 4,6-dihydro-1H-thieno[3,4-c]pyrazol-3-amine (Intermediate 21) and 395 mg (2.01 mmol) of (mesitylmethylene)malononitrile (Intermediate 3) in 5 mL of anhydrous pyridine was stirred at reflux under air overnight (protected from moisture with a calcium sulfate drying tube) and then cooled and concentrated in vacuo. The residue was stirred with 20 mL of methanol and filtered to remove some insoluble material, which was washed with an additional 5 mL of methanol. The combined filtrate and washings were concentrated. Purification of the residue by flash chromatography on silica gel (gradient elution with 5-15% ethyl acetate in hexane) afforded the title compound as a solid. LC-MS 336 (M+1).

Step B 3-(Aminomethyl)-2-mesityl-7H,9H-thieno[3',4':3,4]pyrazolo[1,5-a]pyrimidin-4-amine A suspension of 81 mg (0.24 mmol) of 4-amino-2-mesityl-7H,9H-thieno[3',4':3,4]pyrazolo[1,5-a]pyrimidine-3-carbonitrile from Step A in 1.2 mL of anhydrous tetrahydrofuran was stirred under nitrogen in an ultrasound bath as 1.2 mL (1.2 mmol) of 1M borane-tetrahydrofuran complex in tetrahydrofuran was added gradually by syringe. The mixture was stirred overnight with intermittent sonication. Next, the mixture was quenched by cautious gradual addition of 0.36 mL (4.32 mmol) of concentrated hydrochloric acid (gas evolution) followed by addition of 1.2 mL of methanol. The resulting solution was stirred in a sealed tube with heating in an oil bath at 80° C. for 4 h. The solution was evaporated to dryness and re-concentrated twice from methanol. The residue was converted to free base form by passage through a pre-washed SCX ion exchange cartridge. After flushing the column with methanol to remove trifluoroacetic acid, elution with 1M ammonia in methanol afforded the crude product. Further purification by flash chromatography on silica gel (elution with 98:2:0.4 dichloromethane:methanol:concentrated ammonium hydroxide) yielded the title compound. LC-MS 340 (M+1).

Essentially following the procedures outlined for Examples 1-10, the compounds listed in Tables 2 and 3 were prepared from the intermediates described herein.

TABLE 2

| Example | $R^1$ | Z | Mass Spectrum (M + 1) |
|---|---|---|---|
| 11 | H | 2,4-$Cl_2$—Ph | 309 |
| 12 | Me | 2,4-$Cl_2$—Ph | 323 |
| 13 | $CF_3$ | 2,4-$Cl_2$—Ph | 377 |
| 14 | $HOCH_2$ | 2,4-$Cl_2$—Ph | 339 |
| 15 | cyclopropyl | 2,4-$Cl_2$—Ph | 349 |
| 16 | cyclobutyl | 2,4-$Cl_2$—Ph | 363 |
| 17 | HO | 2,4-$Cl_2$—Ph | 325 |
| 18 | $H_2N$ | 2,4-$Cl_2$—Ph | 324 |
| 19 | morpholin-4-yl | 2,4-$Cl_2$—Ph | 394 |
| 20 | H | 2-F-4-Cl—Ph | 293 |
| 21 | $CF_3$ | 2-F-4-Cl—Ph | 361 |
| 22 | $H_2N$ | 2-F-4-Cl—Ph | 308 |
| 23 | H | 2-Me-4-Cl—Ph | 289 |
| 24 | $CF_3$ | 2-Me-4-Cl—Ph | 357 |
| 25 | $HOCH_2$ | 2-Me-4-Cl—Ph | 319 |
| 26 | $H_2N$ | 2-Me-4-Cl—Ph | 304 |
| 27 | H | 2,4-$Me_2$—Ph | 269 |
| 28 | $CF_3$ | 2,4-$Me_2$—Ph | 337 |
| 29 | $HOCH_2$ | 2,4-$Me_2$—Ph | 299 |
| 30 | cyclopropyl | 2,4-$Me_2$—Ph | 309 |
| 31 | cyclobutyl | 2,4-$Me_2$—Ph | 323 |
| 32 | $H_2N$ | 2,4-$Me_2$—Ph | 284 |
| 33 | MeS | 2,4-$Me_2$—Ph | 315 |
| 34 | $MeSO_2$ | 2,4-$Me_2$—Ph | 347 |
| 35 | H | 2-MeO-4-Cl—Ph | 305 |
| 36 | $CF_3$ | 2-MeO-4-Cl—Ph | 373 |
| 37 | $HOCH_2$ | 2-MeO-4-Cl—Ph | 335 |
| 38 | cyclobutyl | 2-MeO-4-Cl—Ph | 359 |
| 39 | $H_2N$ | 2-MeO-4-Cl—Ph | 320 |
| 40 | H | 2-F-4-$CF_3$—Ph | 327 |
| 41 | $H_2N$ | 5-$Cl_2$-pyridin-2-yl | 325 |
| 42 | $CF_3$ | 2,3-$F_2$-4-Me—Ph | 359 |
| 43 | $H_2N$ | 2,3-$F_2$-4-Me—Ph | 306 |
| 44 | $H_2N$ | 2,4,5-$F_3$—Ph | 310 |
| 45 | H | 2,4,6-$Me_3$—Ph | 283 |
| 46 | $CF_3$ | 2,4,6-$Me_3$—Ph | 351 |
| 47 | $HOCH_2$ | 2,4,6-$Me_3$—Ph | 313 |
| 48 | cyclopropyl | 2,4,6-$Me_3$—Ph | 323 |
| 49 | $H_2N$ | 2,4,6-$Me_3$—Ph | 298 |
| 50 | $Me_2N$ | 2,4,6-$Me_3$—Ph | 326 |
| 51 | MeS | 2,4,6-$Me_3$—Ph | 329 |
| 52 | $Me_2N$ | 2,4,6-$Me_3$—Ph | 326 |
| 53 | H | 2,4,6-$Cl_3$—Ph | 343 |
| 54 | $H_2N$ | 2,4,6-$Cl_3$—Ph | 358 |
| 55 | H | 2,4-$Cl_2$-6-MeO | 339 |
| 56 | $CF_3$ | 2,4-$Cl_2$-6-MeO | 407 |
| 57 | $HOCH_2$ | 2,4-$Cl_2$-6-MeO | 369 |
| 58 | cyclopropyl | 2,4-$Cl_2$-6-MeO | 379 |
| 59 | $H_2N$ | 2,4-$Cl_2$-6-MeO | 354 |

TABLE 3

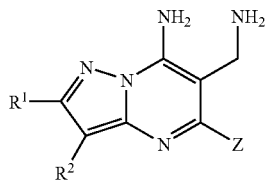

| Example | $R^1$ | $R^2$ | Z | Mass Spectrum (M + 1) |
|---|---|---|---|---|
| 60 | Me | H | 2,4-$Cl_2$—Ph | 322 |
| 61 | H | Ph | 2,4-$Cl_2$—Ph | 384 |
| 62 | H | 2-pyridyl | 2,4-$Cl_2$—Ph | 385 |
| 63 | H | 3-pyridyl | 2,4-$Cl_2$—Ph | 385 |
| 64 | H | 4-pyridyl | 2,4-$Cl_2$—Ph | 385 |
| 65 | H | —Me-thiazol-2-yl | 2,4-$Cl_2$—Ph | 405 |
| 66 | H | $MeSO_2$ | 2,4-$Cl_2$—Ph | 386 |
| 67 | H | Me | 2-F-4-Cl—Ph | 306 |
| 68 | H | $HOCH_2$ | 2-F-4-Cl—Ph | 322 |
| 69 | H | —Me-thiazol-2-yl | 2-F-4-Cl—Ph | 389 |
| 70 | Me | H | 2-Me-4-Cl—Ph | 302 |
| 71 | H | Me | 2-Me-4-Cl—Ph | 302 |
| 72 | H | $EtO_2C$ | 2-Me-4-Cl—Ph | 360 |
| 73 | H | Me | 2,4-$Me_2$—Ph | 282 |
| 74 | H | $EtO_2C$ | 2,4-$Me_2$—Ph | 340 |
| 75 | Me | H | 2-MeO-4-Cl—Ph | 318 |
| 76 | H | Me | 2-MeO-4-Cl—Ph | 318 |
| 77 | H | H | 2,4,6-$Me_3$—Ph | 282 |
| 78 | Me | Me | 2,4,6-$Me_3$—Ph | 310 |
| 79 | H | 2-pyridyl | 2,4,6-$Me_3$—Ph | 359 |
| 80 | H | 4-pyridyl | 2,4,6-$Me_3$—Ph | 359 |
| 81 | H | 5-$Me_2$N-1,3,4-oxadiazol-2-yl | 2,4,6-$Me_3$—Ph | 393 |
| 82 | H | H | 2,4,6-$Cl_3$—Ph | 342 |
| 83 | Me | H | 2,4,6-$Cl_3$—Ph | 356 |
| 84 | H | Me | 2,4,6-$Cl_3$—Ph | 356 |
| 85 | H | $EtO_2C$ | 2,4,6-$Cl_3$—Ph | 414 |
| 86 | H | $MeSO_2$ | 2,4,6-$Cl_3$—Ph | 420 |
| 87 | Me | Cl | 2,4,6-$Me_3$—Ph | 330 |
| 88 | H | $H_2NCH_2$ | 2,4,6-$Me_3$—Ph | 294 [(M-$NH_3$)+1] |
| 89 | H | Me | 2,4-$Cl_2$-6-MeO | 352 |
| 90 | H | MeO | 2,4,6-$Me_3$—Ph | 312 |

EXAMPLE OF A PHARMACEUTICAL FORMULATION

As a specific embodiment of an oral pharmaceutical composition, a 100 mg potency tablet is composed of 100 mg of any of Examples 1-10, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

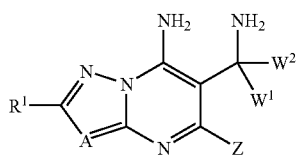

or a pharmaceutically acceptable salt thereof; wherein
each n is independently 0, 1, 2, or 3;
A is $CR^2$;
$W^1$ and $W^2$ are independently H or $C_{1-4}$ alkyl; or $W^1$ and $W^2$ together with the carbon atom to which they are attached form a 3- to 6-membered carbocyclic ring;
Z is phenyl or pyridyl, each of which is substituted with one to five $R^3$ substitutents;
$R^1$ and $R^2$ are each independently selected from the group consisting of:
(1) hydrogen,
(2) $C_{1-10}$ alkyl, wherein alkyl is unsubstituted or substituted with one to five substituents independently selected from:
   (a) halogen,
   (b) hydroxy,
   (c) $OR^4$,
   (d) $SR^4$,
   (e) $S(O)_{1-2}R^4$,
   (f) $SO_2NR^5R^6$,
   (g) $NR^5R^6$,
   (h) $NHSO_2R^4$,
   (i) $N(C_{1-6}\,alkyl)SO_2R^4$,
   (j) $NHCONR^5R^6$,
   (k) $N(C_{1-6}\,alkyl)CONR^5R^6$,
   (l) $NHCO_2R^4$,
   (m) $N(C_{1-6}\,alkyl)CO_2R^4$,
   (n) $OCONR^5R^6$,
   (o) CN,
   (p) $CO_2H$,
   (q) $CO_2C_{1-6}$ alkyl,
   (r) $CONR^5R^6$, and
   (s) phenyl, which is unsubstituted or substituted with one to five substituents independently selected from halogen, CN, OH, $R^4$, $OR^4$, $NHSO_2R^4$, $N(C_{1-6}\,alkyl)SO_2R^4$, $SO_2R^4$, $SO_2NR^5R^6$, $NR^5R^6$, $CONR^5R^6$, $CO_2H$, and $CO_2C_{1-6}$ alkyl,
(3) phenyl, wherein phenyl is unsubstituted or substituted with one to five substituents independently selected from halogen, $R^4$, OH, $OR^4$, $NHSO_2R^4$, $N(C_{1-6}\,alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(4) $(CH_2)_n$-heteroaryl, wherein heteroaryl is unsubstituted or substituted with one to three substituents independently selected from halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(5) $(CH_2)_n$-heterocyclyl, wherein heterocyclyl is unsubstituted or substituted with one to three substituents independently selected from oxo, halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(6) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy, wherein alkyl and alkoxy are unsubstituted or substituted with one to five halogens,
(7) hydroxy,
(8) $OR^4$,
(9) $SR^4$,
(10) $S(O)_{1-2}R^4$,
(11) $SO_2NR^5R^6$,
(12) $NR^5R^6$,
(13) $NHSO_2R^4$,
(14) $N(C_{1-6}\,alkyl)SO_2R^4$,
(15) $NHCONR^5R^6$,
(16) $N(C_{1-6}\,alkyl)CONR^5R^6$,
(17) $NHCO_2R^4$,
(18) $N(C_{1-6}\,alkyl)CO_2R^4$,
(19) $OCONR^5R^6$,
(20) CN,
(21) $CO_2H$,
(22) $CO_2C_{1-6}$ alkyl,
(23) $CONR^5R^6$, and
(24) halogen;
each $R^3$ is independently selected from the group consisting of:
(1) halogen,
(2) $C_{1-6}$ alkyl, unsubstituted or substituted with one to five substituents independently selected from halogen, hydroxy, and $C_{1-4}$ alkoxy,
(3) $C_{1-6}$ alkoxy, unsubstituted or substituted with one to five substituents independently selected from halogen, hydroxy, and $C_{1-4}$ alkoxy,
(4) hydroxy,
(5) $O(CH_2)_n$-aryl, wherein aryl is unsubstituted or substituted with one to five substituents independently selected from halogen, methyl, hydroxy, and methoxy, and
(6) $O(CH_2)_n$-heteroaryl, wherein heteroaryl is unsubstituted or substituted with one to five substituents independently selected from halogen, methyl, hydroxy, and methoxy;
$R^4$ is $C_{1-6}$ alkyl, unsubstituted or substituted with one to five substituents independently selected from halogen, hydroxy, methoxy, $CO_2H$, and $CO_2C_{1-6}$ alkyl; and
$R^5$ and $R^6$ are each independently selected from the group consisting of:
(1) hydrogen,
(2) $C_{1-6}$ alkyl, unsubstituted or substituted with one to five substituents independently selected from halogen, hydroxy, and $C_{1-6}$ alkoxy,
(3) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$alkoxy, wherein alkyl and alkoxy are unsubstituted or substituted with one to five halogens, and
(4) $(CH_2)_n$-phenyl, wherein phenyl is unsubstituted or substituted with substituents independently selected from halogen, OH, $C_{1-6}$ alkyl, and $C_{1-6}$ alkoxy, wherein alkyl and alkoxy are unsubstituted or substituted with one to five halogens;
or wherein $R^5$ and $R^6$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

2. The compound of claim 1 wherein $W^1$ and $W^2$ are H.

3. The compound of claim 2 wherein Z is phenyl phenyl which is substituted with two to five $R^3$ substituents; each n is independently 0, 1, 2, or 3;
$R^1$ is selected from the group consisting of:
  (1) hydrogen,
  (2) $C_{1-4}$ alkyl, wherein alkyl is unsubstituted or substituted with one to five substituents independently selected from:
    (a) halogen,
    (b) hydroxy,
    (c) $OR^4$,
    (d) $SR^4$, and
    (e) $NR^5R^6$,
  (3) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy,
  (4) hydroxy,
  (5) $OR^4$,
  (6) $SR^4$, and
  (7) $NR^5R^6$;
$R^2$ is selected from the group consisting of:
  (1) hydrogen,
  (2) $C_{1-10}$ alkyl, wherein alkyl is unsubstituted or substituted with one to five substituents independently selected from:
    (a) halogen,
    (b) hydroxy,
    (c) $OR^4$,
    (d) $SR^4$,
    (e) $S(O)_{1-2}R^4$,
    (f) $SO_2NR^5R^6$,
    (g) $NR^5R^6$,
    (h) $NHSO_2R^4$,
    (i) $N(C_{1-6}alkyl)SO_2R^4$,
    (j) $NHCONR^5R^6$,
    (k) $N(C_{1-6}$ alkyl$)CONR^5R^6$,
    (l) $NHCO_2R^4$,
    (m) $N(C_{1-6}$ alkyl$)CO_2R^4$,
    (n) $OCONR^5R^6$,
    (o) CN,
    (p) $CO_2H$,
    (q) $CO_2C_{1-6}$ alkyl,
    (r) $CONR^5R^6$, and
    (s) phenyl, which is unsubstituted or substituted with one to five substituents independently selected from halogen, CN, OH, $R^4$, $OR^4$, $NHSO_2R^4$, $N(C_{1-6}$ alkyl$)SO_2R^4$, $SO_2R^4$, $SO_2NR^5R^6$, $NR^5R^6$, $CONR^5R^6$, $CO_2H$, and $CO_2C_{1-6}$ alkyl,
  (3) phenyl which is unsubstituted or substituted with one to five substituents independently selected from halogen, $R^4$, OH, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
  (4) $(CH_2)_n$-heteroaryl, wherein heteroaryl is unsubstituted or substituted with one to three substituents independently selected from halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
  (5) $(CH_2)_n$-heterocyclyl, wherein heterocyclyl is unsubstituted or substituted with one to three substituents independently selected from oxo, halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
  (6) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy, wherein alkyl and alkoxy are unsubstituted or substituted with one to five halogens,
  (7) hydroxy,
  (8) $OR^4$,
  (9) $SR^4$,
  (10) $S(O)_{1-2}R^4$,
  (11) $SO_2NR^5R^6$,
  (12) $NR^5R^6$,
  (13) $NHSO_2R^4$,
  (14) $N(C_{1-6}alkyl)SO_2R^4$,
  (15) $NHCONR^5R^6$,
  (16) $N(C_{1-6}$ alkyl$)CONR^5R^6$,
  (17) $NHCO_2R^4$,
  (18) $N(C_{1-6}$ alkyl$)CO_2R^4$,
  (19) $OCONR^5R^6$,
  (20) CN,
  (21) $CO_2H$,
  (22) $CO_2C_{1-6}$ alkyl,
  (23) $CONR^5R^6$, and
  (24) halogen;
each $R^3$ is independently selected from the group consisting of:
  (1) halogen,
  (2) $C_{1-4}$ alkyl, unsubstituted or substituted with one to five substituents independently selected from halogen, hydroxy, and $C_{1-4}$ alkoxy,
  (3) $C_{1-4}$ alkoxy, unsubstituted or substituted with one to five substituents independently selected from halogen, hydroxy, and $C_{1-4}$ alkoxy,
  (4) hydroxy,
  (5) $O(CH_2)_n$-aryl, wherein aryl is unsubstituted or substituted with one to five substituents independently selected from halogen, methyl, hydroxy, and methoxy, and
  (6) $O(CH_2)_n$-heteroaryl, wherein heteroaryl is unsubstituted or substituted with one to five substituents independently selected from halogen, methyl, hydroxy, and methoxy;
$R^4$ is $C_{1-6}$ alkyl, unsubstituted or substituted with one to five substituents independently selected from halogen, hydroxy, and methoxy; and
$R^5$ and $R^6$ are independently selected from the group consisting of:
  (1) hydrogen,
  (2) $C_{1-4}$ alkyl, unsubstituted or substituted with one to five substituents independently selected from halogen, hydroxy, and $C_{1-4}$ alkoxy, and
  (3) $(CH_2)_n$—$C_{3-6}$ cycloalkyl, wherein cycloalkyl is unsubstituted or substituted with one to five substituents independently selected from halogen, OH, $C_{1-4}$ alkyl, and $C_{1-4}$ alkoxy, wherein alkyl and alkoxy are unsubstituted or substituted with one to five halogens;
or wherein $R^5$ and $R^6$ together with the nitrogen atom to which they are attached form a heterocyclic ring selected from azetidine, pyrrolidine, piperidine, piperazine, and morpholine.

4. The compound of claim 1 of the structural formula Ic:

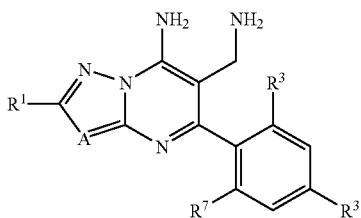

Ic wherein each n is independently 0, 1, 2, or 3;
A is $CR^2$;
$R^3$ is chloro or methyl, which is unsubstituted or substituted with one to three fluorine atoms;
$R^7$ is selected from the group consisting of:
(1) hydrogen,
(2) halogen,
(3) $C_{1-6}$ alkyl, unsubstituted or substituted with one to five substituents independently selected from halogen, hydroxy, and $C_{1-4}$ alkoxy,
(4) $C_{1-6}$ alkoxy, unsubstituted or substituted with one to five substituents independently selected from halogen, hydroxy, and $C_{1-4}$ alkoxy,
(5) hydroxy,
(6) $O(CH_2)_n$-aryl, wherein aryl is unsubstituted or substituted with one to five substituents independently selected from halogen, methyl, hydroxyl, and methoxy, and
(7) $O(CH_2)_n$-heteroaryl, wherein heteroaryl is unsubstituted or substituted with one to five substituents independently selected from halogen, methyl, hydroxyl, and methoxy;
$R^1$ is selected from the group consisting of:
(1) hydrogen,
(2) $C_{1-4}$ alkyl, wherein alkyl is unsubstituted or substituted with one to five substituents independently selected from:
 (a) halogen,
 (b) hydroxy,
 (c) $OR^4$,
 (d) $SR^4$, and
 (e) $NR^5R^6$,
(3) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy,
(4) hydroxy,
(5) $OR^4$,
(6) $SR^4$, and
(7) $NR^5R^6$; and
$R^2$ is selected from the group consisting of:
(1) hydrogen,
(2) $C_{1-10}$ alkyl, wherein alkyl is unsubstituted or substituted with one to five substituents independently selected from:
 (a) halogen,
 (b) hydroxy,
 (c) $OR^4$,
 (d) $SR^4$,
 (e) $S(O)_{1-2}R^4$,
 (f) $SO_2NR^5R^6$,
 (g) $NR^5R^6$,
 (h) $NHSO_2R^4$,
 (i) $N(C_{1-6}alkyl)SO_2R^4$,
 (j) $NHCONR^5R^6$,
 (k) $N(C_{1-6} alkyl)CONR^5R^6$,
 (l) $NHCO_2R^4$,
 (m) $N(C_{1-6} alkyl)CO_2R^4$,
 (n) $OCONR^5R^6$,
 (o) CN,
 (p) $CO_2H$,
 (q) $CO_2C_{1-6}$ alkyl,
 (r) $CONR^5R^6$, and
 (s) phenyl, which is unsubstituted or substituted with one to five substituents independently selected from halogen, CN, OH, $R^4$, $OR^4$, $NHSO_2R^4$, $N(C_{1-6} alkyl)SO_2R^4$, $SO_2R^4$, $SO_2NR^5R^6$, $NR^5R^6$, $CONR^5R^6$, $CO_2H$, and $CO_2C_{1-6}$ alkyl,
(3) phenyl which is unsubstituted or substituted with one to five substituents independently selected from halogen, $R^4$, OH, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(4) $(CH_2)_n$-heteroaryl, wherein heteroaryl is unsubstituted or substituted with one to three substituents independently selected from halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(5) $(CH_2)_n$-heterocyclyl, wherein heterocyclyl is unsubstituted or substituted with one to three substituents independently selected from oxo, halogen, OH, $R^4$, $OR^4$, $NHSO_2R^4$, $N(C_{1-6}alkyl)SO_2R^4$, $SO_2R^4$, $SO_2NR^5R^6$, $NR^5R^6$, $CONR^5R^6$, CN, $CO_2H$, and $CO_2C_{1-6}$ alkyl,
(6) $(CH_2)_n$—$C_{3-6}$ cycloalkyl, wherein cycloalkyl is unsubstituted or substituted with one to five substituents independently selected from halogen, OH, $C_{1-6}$ alkyl, and $C_{1-6}$ alkoxy, wherein alkyl and alkoxy are unsubstituted or substituted with one to five halogens,
(7) hydroxy,
(8) $OR^4$,
(9) $SR^4$,
(10) $S(O)_{1-2}R^4$,
(11) $SO_2NR^5R^6$,
(12) $NR^5R^6$,
(13) $NHSO_2R^4$,
(14) $N(C_{1-6}alkyl)SO_2R^4$,
(15) $NHCONR^5R^6$,
(16) $N(C_{1-6} alkyl)CONR^5R^6$,
(17) $NHCO_2R^4$,
(18) $N(C_{1-6} alkyl)CO_2R^4$,
(19) $OCONR^5R^6$,
(20) CN,
(21) $CO_2H$,
(22) $CO_2C_{1-6}$ alkyl,
(23) $CONR^5R^6$, and
(24) halogen.

5. The compound of claim 1 which is selected from the group consisting of:

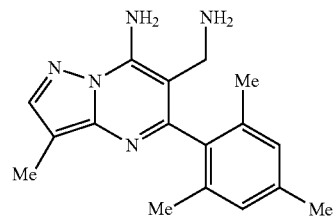

-continued

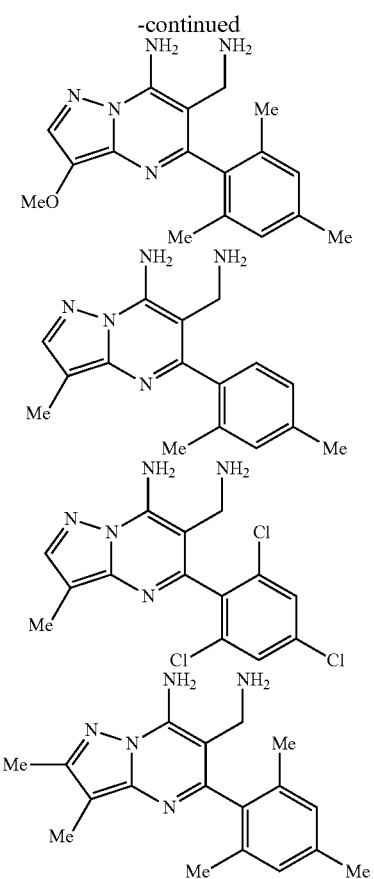

-continued

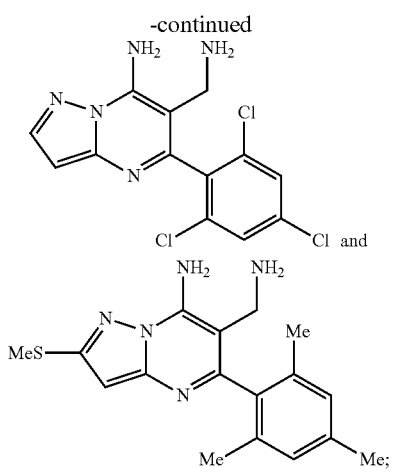

or a pharmaceutically acceptable salt thereof.

6. A pharmaceutical composition which comprises a compound of claim 1 and a pharmaceutically acceptable carrier.

7. The pharmaceutical composition of claim 6 additionally comprising metformin.

8. A method for treating non-insulin dependent (Type 2) diabetes in a mammal in need thereof which comprises the administration to the mammal of a therapeutically effective amount of a compound of claim 1.

\* \* \* \* \*